US012766221B2

United States Patent

(12) United States Patent
Han et al.

(10) Patent No.: US 12,766,221 B2
(45) Date of Patent: Oct. 20, 2026

(54) INJECTABLE, CROSS-LINKABLE AND SUBCELLULAR SIZE MICROFIBERS FOR SOFT TISSUE REPAIR

(71) Applicants: Drexel University, Philadelphia, PA (US); The Children's Hospital of Philadelphia, Philadelphia, PA (US)

(72) Inventors: Li-Hsin Han, Wynnewood, PA (US); Mingkun Wang, Philadelphia, PA (US); Chunxiao Cui, Arlington, MA (US); John Todd Lawrence, Wynnewood, PA (US); Maurizio Pacifici, Philadelphia, PA (US)

(73) Assignees: Thomas Jefferson University, Philadelphia, PA (US); The Children's Hospital of Philadelphia, Philadelphia, PA (US)

(*) Notice: Subject to any disclaimer, the term of this patent is extended or adjusted under 35 U.S.C. 154(b) by 690 days.

(21) Appl. No.: 18/265,818

(22) PCT Filed: Dec. 17, 2021

(86) PCT No.: PCT/US2021/064013
§ 371 (c)(1),
(2) Date: Jun. 7, 2023

(87) PCT Pub. No.: WO2022/133201
PCT Pub. Date: Jun. 23, 2022

(65) Prior Publication Data

US 2024/0033401 A1 Feb. 1, 2024

Related U.S. Application Data

(60) Provisional application No. 63/127,440, filed on Dec. 18, 2020.

(51) Int. Cl.
*A61L 27/26* (2006.01)
*A61L 27/38* (2006.01)
*A61L 27/56* (2006.01)

(52) U.S. Cl.
CPC ........... *A61L 27/26* (2013.01); *A61L 27/3817* (2013.01); *A61L 27/3834* (2013.01); *A61L 27/3847* (2013.01); *A61L 27/3852* (2013.01); *A61L 27/3856* (2013.01); *A61L 27/56* (2013.01); *A61L 2300/60* (2013.01);
(Continued)

(58) Field of Classification Search
CPC ........................................................ A61L 27/26
See application file for complete search history.

(56) References Cited

U.S. PATENT DOCUMENTS 10,837,131 B2 11/2020 Han et al.
2009/0175944 A1 7/2009 Ringeisen et al.
(Continued)

OTHER PUBLICATIONS

Maude Gluais et al. "In vitro and in vivo evaluation of an electrospun-aligned microfibrous implant for Annulus fibrosus repair." Biomaterials, vol. 205 (2019) pp. 81-93. (Year: 2019).*
(Continued)

*Primary Examiner* — Isaac Shomer
(74) *Attorney, Agent, or Firm* — Saul Ewing LLP; Kathryn Doyle; Justin Crotty

(57) ABSTRACT

The present invention provides an injectable scaffold comprising a plurality of unclad microfibers, and a diluent solution.

11 Claims, 18 Drawing Sheets

(52) U.S. Cl.
CPC ....... *A61L 2400/06* (2013.01); *A61L 2430/02* (2013.01); *A61L 2430/06* (2013.01); *A61L 2430/38* (2013.01)

(56) References Cited

U.S. PATENT DOCUMENTS

| | | | | |
|---|---|---|---|---|
| 2011/0274742 | A1 | 11/2011 | Arinzeh et al. | |
| 2012/0063997 | A1 | 3/2012 | Hunter et al. | |
| 2016/0346427 | A1 | 12/2016 | Nunes et al. | |
| 2018/0171513 | A1 * | 6/2018 | Han | B29C 53/04 |
| 2018/0339084 | A1 | 11/2018 | Bellas et al. | |
| 2019/0076373 | A1 | 3/2019 | Bencherif et al. | |
| 2020/0069846 | A1 | 3/2020 | Martin et al. | |
| 2020/0215228 | A1 | 7/2020 | Coulombe et al. | |

OTHER PUBLICATIONS

Junchuan Yang et al. "Biomimetic nanofibers can construct effective tissue-engineered intervertebral discs for therapeutic implantation." Nanoscale, vol. 9, 2017, pp. 13095-13103. (Year: 2017).*
International Search Report and Written Opinion dated Mar. 7, 2022 for International Appln. No. PCT/ US2021/064013. (Year: 2022).*
"International Search Report and Written Opinion dated Mar. 7, 2022 for International Appln. No. PCT/US2021/064013".

* cited by examiner

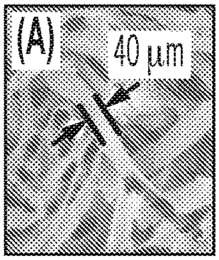
FIG. 2A
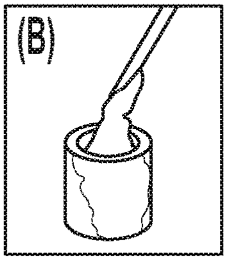
FIG. 2B
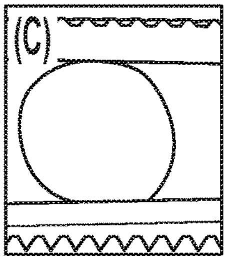
FIG. 2C
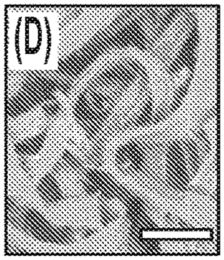
FIG. 2D
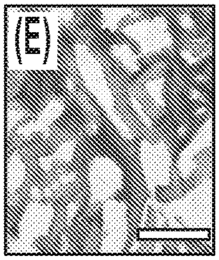
FIG. 2E
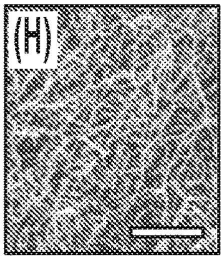
FIG. 2H
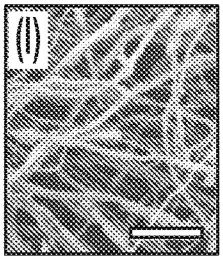
FIG. 2I
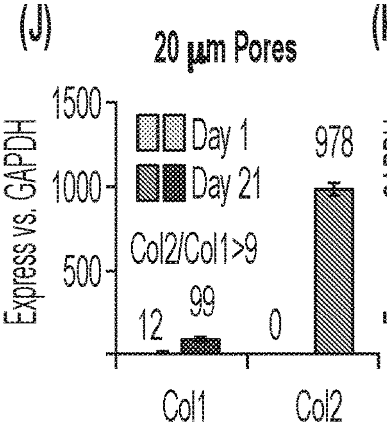
FIG. 2J
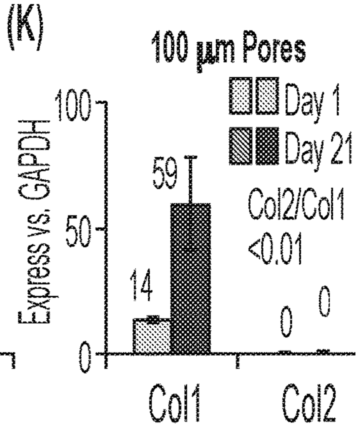
FIG. 2K
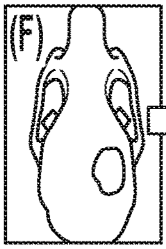
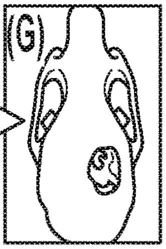
FIG. 2F FIG. 2G
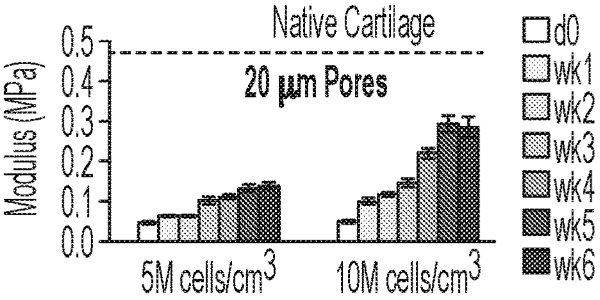
FIG. 2L

INJECTABLE, CROSS-LINKABLE AND SUBCELLULAR SIZE MICROFIBERS FOR SOFT TISSUE REPAIR

CROSS-REFERENCE TO RELATED APPLICATIONS

This application is a 35 U.S.C. § 371 national phase application from, and claims priority to, International Application No. PCT/US2021/064013, filed Dec. 17, 2021, which claims priority under 35 U.S.C. § 119 (e) to U.S. Provisional Patent Application 63/127,440, filed Dec. 18, 2020, all of which applications are incorporated by reference herein in their entireties.

BACKGROUND OF THE INVENTION

Soft tissues injuries and degeneration is a serious health problem in the world. In the United States, Intervertebral Disk Degeneration (IVD) affects approximately 30 million people every year. Osteoarthritis affects more than 27 million people and is predicted to affect 1 in 2 individuals in their lifetime. Treatments for these diseases command a large percentage of the total overall health care budget in the United States. Surgical interventions are needed to restore soft tissues integrity and prevent further tissues deterioration. Unfortunately, none of the currently available treatments are ideal. In the case of IVD for example, annulus fibrosus repair has been attempted using suturing and annuloplasty techniques. Injections of stem cells into the nucleus pulposus are being used to treat degenerative IVD. However, these techniques failed to improve annular strength. In the case of knee cartilage, microfracture of the bone at the base of a lesion to allow stem cells to enter the space is one of the most commonly performed procedures for this condition. While this is a single stage procedure, it induces the formation of cartilage scar that is not as resilient as native hyaline cartilage and is more prone to breakdown over time. Autologous Chondrocyte Implantation (ACI), which fills cartilage defects with chondrocytes that have been expanded in culture, is considered the gold standard for repair. However, this is a two-stage procedure and requires an invasive operation. Even though this procedure can result in healing tissue more like native hyaline cartilage, it has not shown significant clinical advantages over microfracture.

There is therefore a need in the art for improved compositions and methods for repairing tissue and the present invention addresses this need.

SUMMARY OF THE INVENTION

In one aspect, the invention provides an injectable scaffold comprising a plurality of unclad microfibers and a diluent solution.

In another aspect, the invention provides a method of repairing a soft tissue defect, in a subject, wherein the method comprises obtaining a microfiber stretch-and-fold ring comprising a plurality of microfibers and a cladding, shaving the stretch-and-fold ring into a plurality of chips, dissolving the cladding from the chips by contacting the chips with the uncladding solution to unclad the microfibers, hydrating the uncladded microfibers with a hydrating solution, thereby forming a paste, introducing a plurality of cells into the paste, thereby forming a seeded paste, loading the seeded paste into a syringe, and injecting the seeded paste into a region of interest.

In yet another aspect, the invention provides a kit comprising the injectable scaffold as described elsewhere herein, a plurality of cells in solution, and a sterile syringe and needle.

In certain embodiments, the microfibers comprise unclad shavings from a shaved stretch-and-fold ring comprising a plurality of microfibers clad in a sheath.

In certain embodiments, the microfibers are gelatin microfibers.

In certain embodiments, the microfibers comprise one or more selected from the group consisting of: natural polymers, synthetic polymers, and combinations thereof.

In certain embodiments, the natural polymers comprise one or more selected from the group consisting of: gelatin, collagen, elastin, fibrin, fibrinogen, laminin, dextran, silk protein, chitosan, alginate, heparin, heparin sulfate, and laminin, and combinations thereof.

In certain embodiments, the synthetic polymers comprise one or more selected from the group consisting of: polyethylene glycol, polycaprolactone, polylactic acid, polyglycolic acid, polylactic-glycolic acid, Teflon™, Nylon™, polycarbonate, polyamide, polystyrene, polypropylene, polyester, and combinations thereof.

In certain embodiments, the plurality of microfibers comprises microfibers having a uniform diameter. In certain embodiments, the diameter of each microfiber varies from about 0.1 μm to about 100 μm.

In certain embodiments, the scaffold comprises pores that are about 5 times to about 10 times larger than the diameter of the microfibers forming the scaffold.

In certain embodiments, the cladding comprises polycaprolactone (PCL) cladding.

In certain embodiments, the uncladding solution comprises one or more selected from the group consisting of: acetone, chloroform, hexane, ethanol, methanol, pentane, methylcyclohexane, ethane, dimethyl sulfoxide, ethyl ether, perfluoropentane, perfluoromethylcyclohexane, hexafluoroethane, perfluoro-1,3-dimethylcyclohexane, perfluoromethyldecalin, and/or combinations thereof.

In certain embodiments, the method of repairing a soft tissue defect comprises crosslinking the seeded paste.

In certain embodiments, the crosslinking comprises crosslinking with one or more selected from the group consisting of: visible light, UV light, glutaraldehyde, BDDE, enzymes, click chemistry, and combinations thereof.

In certain embodiments, solution comprises one or more selected from the group consisting of: saline, media, buffered saline, phosphate-buffered saline, sterile water, and/or combinations thereof.

In certain embodiments, wherein the plurality of cells comprises one or more selected from the group consisting of: chondrocytes, pluripotent cells, stem cells, fibroblasts.

In certain embodiments, the seeded paste is injected using a 22 g needle.

In certain embodiments, the chips have a thickness of about 200 μm.

In certain embodiments, the chips have a length of from about 200 μm to about 5000 μm.

In certain embodiments, the subject is a mammal.

In certain embodiments, the subject is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A demonstrates that cartilage repair techniques often form fibrocartilage that is weak and prone to breakdown over time. FIG. 1C illustrates autologous chondrocyte implantation (ACI) which requires open surgery in the joint and has not shown significant clinical advantages over microfracture (FIG. 1B); FIG. 1D depicts matrix-assisted ACI, which aims to promote hyaline cartilage formation, requires open knee surgery. Shown in FIG. 1E, current IVD repairs are mostly based on therapeutic cells injection (into the nucleus pulposus) or discs replacement (by cell-seeded scaffolds); the common drawbacks of the existing methods for soft tissue repairs are the need for open surgeries (shown in FIG. 1F), poor integration due to geometry mismatch (shown in FIG. 1G), and the lack of effective methods to control cellular environment and provide the needed biophysical properties, such as optimal porosity, to induce desired cell activities for soft tissues production, shown in FIG. 1H.

FIGS. 2A-2L illustrate features of exemplary injectable scaffold compositions for soft tissue repair, as contemplated herein. The injectable scaffold compositions possess fusible microfibers that form cell-sized porosity, depicted in FIG. 2A, are needle-injectable (FIG. 2B), and form solid scaffolds via fiber crosslinking (FIG. 2C). Cells in Fiber-Gel have space to expand to create cartilage (demonstrated in FIGS. 2D and 2E). FIGS. 2F and 2G depict results from a safety and tissue engineering assay using a mouse cranial defect model. FIGS. 2H-2L depict efficacy data for supporting chondrogenesis.

FIG. 5A depicts preparing a ring-shaped precursor with a core of fiber material and a sheath of pseudo-plastic material. FIG. 5B depicts pulling and thinning the ring diameter while doubling the length; and FIGS. 5C-5D depict folding the ring and recovering the ring diameter while doubling the core number. Repeating the steps depicted in FIGS. 5B, 5C, and 5D for N times increases the core number exponentially by a factor of 2N and reduces the core diameter exponentially by a factor of 20.5N. Fibers are recovered from the ring by dissolving the sheath. Sub-figures below FIGS. 5A, 5B and 5D illustrate ring cross-sections.

FIGS. 7C and 7E are SEM images; scale bars are 200 μm.

FIG. 9C depicts microCT images showing that fiber-based scaffolds accelerated bone regeneration and almost filled up the defects by week 6, yet minimal bone formation was observed in hydrogel-based implants.

FIGS. 10A-10D depict stretch-and-fold method for generating a micro/nanoscale c-fiber preparation. FIG. 10E show a segment of cladded micro/nano fiber. FIG. 10F show dissolution of cladding. FIGS. 10G and H show the fibers obtained after the cladding is dissolved. FIG. 10I shows the fiber paste and FIG. 10J show cross-linking of microfibers. Scale bars for FIGS. 10G and 10H is 100 μm.

DETAILED DESCRIPTION

Definitions

Figures 1A, 1B, 1C, 1D:
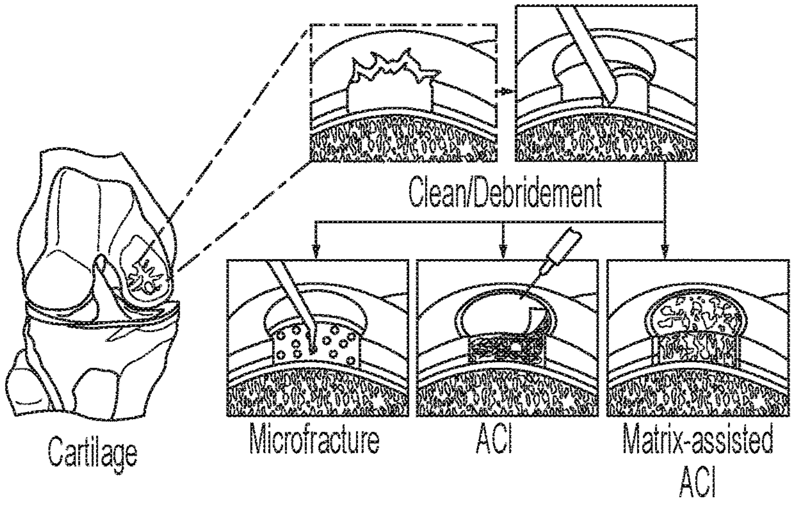
FIGS. 1A-1H depict the limitations of surgical interventions used to restore soft tissue integrity and prevent further tissues deterioration.
Figure 1F:
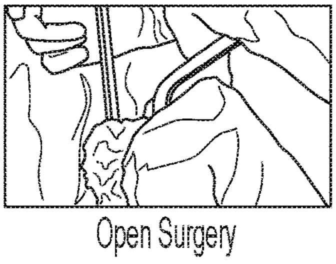
Figure 1E:
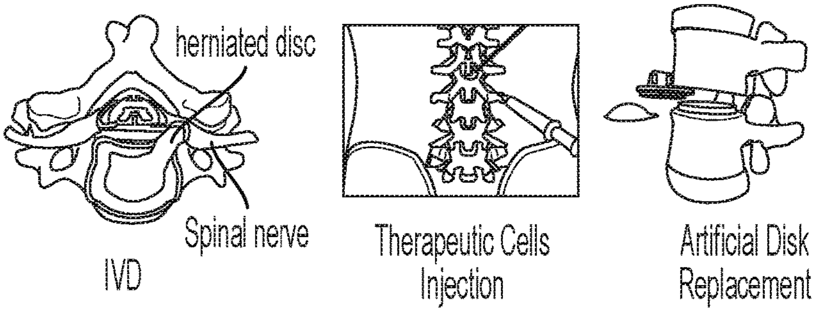
Figure 1G:
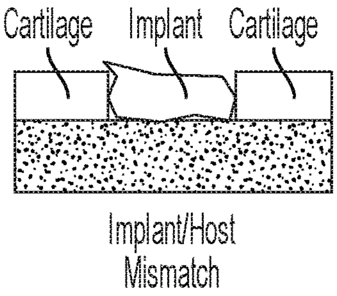
Figure 1H:
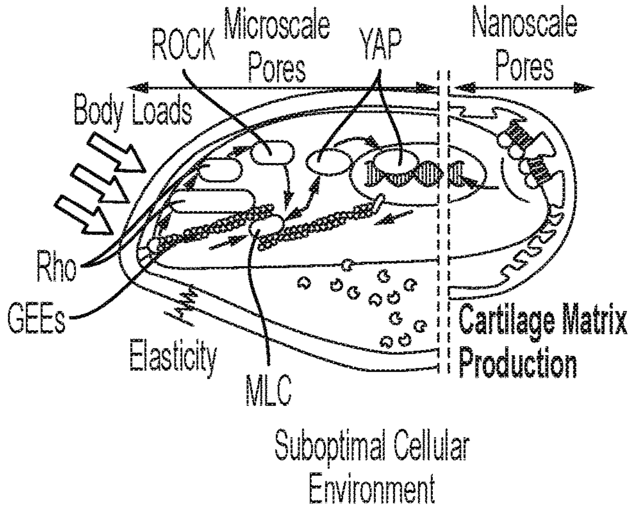
Figure 3A:
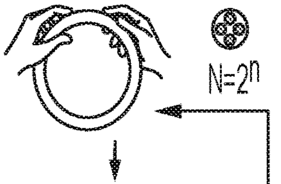
FIGS. 3A-3G depict an exemplary "stretch-and-fold" method used in the present invention. The steps include the following: Preparing a ring-shaped precursor with a core of fiber material and a cladding of pseudo-plastic material (FIG. 3A); Repeatedly pulling and thinning the ring diameter, doubling the length, folding the ring, recovering the ring diameter while doubling the core number (FIGS. 3B and 3C); Repeating the steps shown in FIGS. 3A, 3B, and 3C for n times increases the core number exponentially by a factor of 2n and reduces the core diameter exponentially by a factor of 20.5n. To enable injectability, the microfibers are chopped, with the cladding, by a slicing tool into short fibers that are about 200 μm long (FIG. 3D). Hydrating these microfibers with PBS or cell culture media turns the microfibers into a paste that can be delivered through a 22-gauge or thicker needle. Microfibers are recovered from the ring by dissolving the cladding (FIG. 3E). Resulting fibers can be mixed with cells and delivered via a syringe (FIG. 3F, 3G).
Figure 3B:
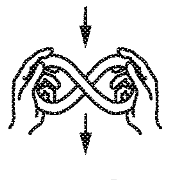
Figure 3C:
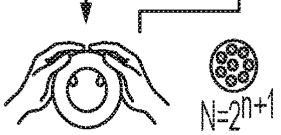
Figure 3D:
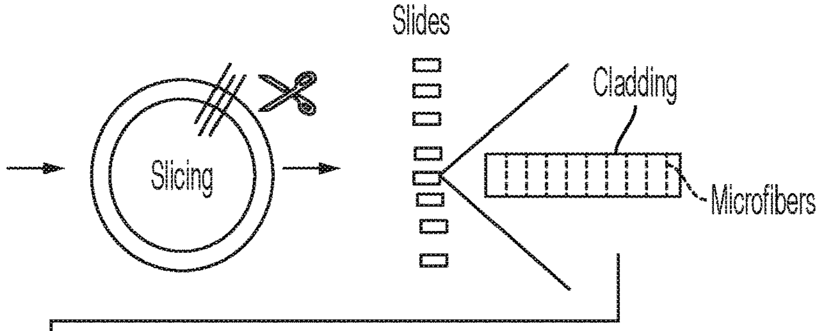
Figure 3E:
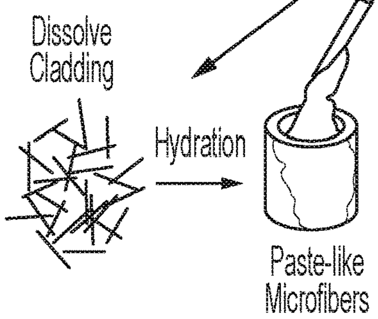
Figure 3F:
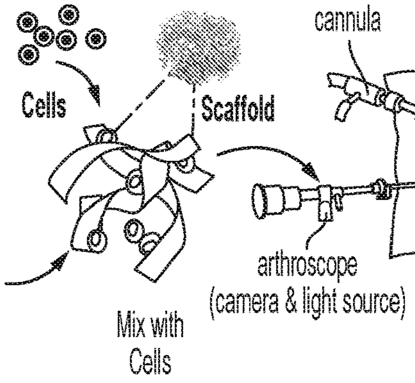
Figure 3G:
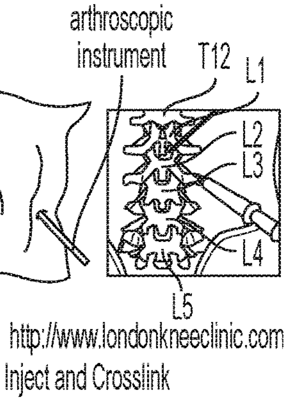
Figure 4A:
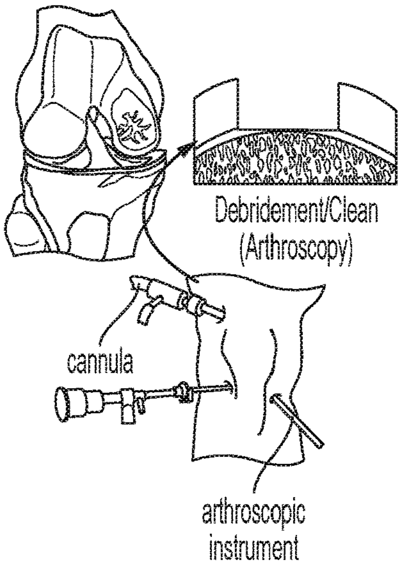
FIGS. 4A-4D depicts an exemplary injectable scaffold used for soft tissue repair. A physician uses a needle to inject the injectable scaffold that has been mixed with therapeutic cells into a targeted tissue during arthroscopy (FIGS. 4A-4B), or any other minimally invasive setting, and completely fills an arbitrary soft tissue defect (FIG. 4C). The injectable scaffold can be crosslinked into a solid scaffold by fibrin glue (FIG. 4D). Alternatively, the injectable scaffold can be crosslinked by UV or blue light delivered via the fiber optics of an arthroscope.
Figures 4B, 4C:
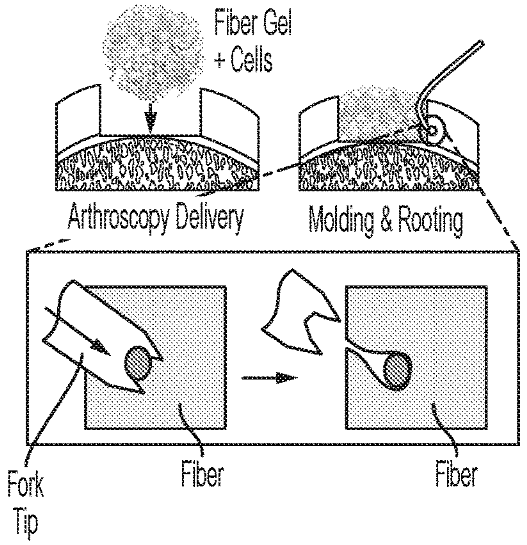
Figure 4D:
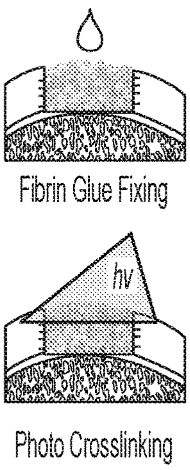

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "clad" or "cladding" refers to application of one material over another to provide a skin or layer, while the term "unclad" or "uncladding" refers to removal of the skin or the layer.

As used herein, the term FiberGel refers to microfibers of the invention in paste-like consistency.

The terms "patient," "subject," or "individual" are used interchangeably herein, and refer to any animal, or cells thereof whether in vitro or in situ, amenable to the methods described herein. In a non-limiting embodiment, the patient, subject, or individual is a human.

As used herein, the term "repairing" or "treatment" or "treating" is defined as the application or administration of a therapeutic agent, i.e., a compound of the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides one or more phase-transformable, injectable scaffolds for correcting a defect in a tissue in a subject. The present invention further relates to methods for correcting a tissue defect in a subject. In certain embodiments, the subject is a human subject.

Injectable Scaffolds

In one aspect, the present invention provides an injectable scaffold. The injectable scaffold comprises one or more unclad microfibers and a diluent solution. The injectable scaffold comprises phase-transformable scaffolds. That is, the injectable scaffolds can transform from solid phase to liquid phase, liquid phase to solid phase, and/or sequential combinations thereof. The injectable scaffold can be in a liquid form, a solid form, a paste-like form, and or combinations thereof.

The one or more unclad microfibers comprise one or more unclad microfibers formed from one or more microfiber rings fabricated using a stretch-and-fold method as described in U.S. patent application Ser. No. 15/816,639, which is incorporated herein by reference in its entirety. The microfibers as described herein are cut, shaved, chopped, or otherwise partitioned from one or more microfiber rings clad in a sheath. The microfibers are then unclad using one or more uncladding solutions and/or solvents. The one or more uncladding solutions and/or solvents may comprise one or more organic solvents such as acetone, chloroform, hexane, ethanol, methanol, pentane, methylcyclohexane, ethane, dimethyl sulfoxide, ethyl ether, perfluoropentane, perfluoromethylcyclohexane, hexafluoroethane, perfluoro-1,3-dimethylcyclohexane, perfluoromethyldecalin, and the like. The unclad microfibers can be hydrated using one or more aqueous solutions such as phosphate-buffered saline (PBS), cell culture media, water, isotonic saline solution, and the like.

The injectable scaffold is formed from the microfibers having approximately same length and diameter. The unclad microfibers can have a length of up to about 10 μm, about 10 μm to about 25 μm, about 25 μm to about 50 μm, about 50 μm to about 75 μm, about 75 μm to about 100 μm, about 100 μm to about 125 μm, about 125 μm to about 150 μm, about 150 μm to about 175 μm, about 175 μm to about 200 μm, about 200 μm to about 500 μm, and so on. The unclad microfibers can have a diameter of about 0.1 μm to about 100 μm. The unclad microfibers can have a diameter of about 0.1, 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, or about 100 μm. The unclad microfibers may be in a solid phase, a liquid phase, and/or a paste having both solid and liquid phases. The unclad microfibers can have a cross-sectional shape including, for example, square, triangle, rectangle, semi-circle, diamond, hexagon, pentagon, octagon, and the like. In some embodiments, the microfibers have compartments made of different materials, where the compartments have one or more geometries including but not limited to co-axis cylinders, co-axis polygon, bi-layered beam, radially organized compartments, and the like.

The microfibers are formed from any suitable material including any suitable natural polymer, synthetic polymer, and/or combinations thereof. The microfibers can be formed from one or more natural polymers including gelatin, collagen, elastin, fibrin, fibrinogen, laminin, dextran, silk protein, chitosan, alginate, heparin, heparin sulfate, and laminin, and/or combinations thereof. The microfibers can be formed from one or more synthetic polymers including one or more of polyethylene glycol, polycaprolactone, polylactic acid, polyglycolic acid, polylactic-glycolic acid, Teflon™, Nylon™, polycarbonate, polyamide, polystyrene, polypropylene, polyester, and/or combinations thereof.

Embodiments of the microfibers are biocompatible and/or mixable with cells. For example, the unclad microfibers can be mixed with cells including soft tissue cells, connective tissue cells, muscle cells, bone cells and the like. The cells can include chondrocytes, osteocytes, osteoblasts, osteoclasts, fibrocytes, fibroblasts, myocytes, adipocytes, mesenchymal cells, epithelial cells, endothelial cells, synovial stem cells, adipose-derived stem cells, bone marrow-derived cells including bone marrow-derived stem cells, embryonic stem cells, mesenchymal stem cells, autologous chondrocytes, joint interzone cells, neonatal chondrocytes, allograph chondrocytes, xenograft chondrocytes, cells derived from platelet-rich plasma, cells derived from subchondral blood, cells isolated from blood from subchondral drilling, and the like.

Embodiments of the unclad microfibers solidify into a scaffold. The scaffold can have pores with size or range of sizes optimal for a particular tissue of interest. Scaffolds have controlled pore or channel size that is roughly five to ten times of the diameter of the individual microfibers. The porosity can be optimized in order to provide preferred tissue mechanics, cell growth, cell proliferation, and the like. For example, the scaffold can have a porosity that provides sufficient rigidity, elasticity, tensile strength, compressibility, and the like, in order to mimic the mechanics of in vivo tissue. The pore size of the scaffold can include up to about 100 nm, about 100 nm to about 200 nm, about 200 nm to about 400 nm, about 400 nm to about 600 nm, about 600 nm to about 800 nm, about 800 nm to about 1 μm, about 1 μm to about 10 μm, about 10 to about 50 μm, about 50 to about 100 μm, about 100 to about 150 μm, about 150 μm to about 200 μm, about 200 μm to about 250 μm, about 250 μm to about 300 μm, about 350 am, about 350 μm to about 400 am, about 400 μm to about 450 am, about 450 μm to about 500 am, and the like.

The injectable scaffolds can further include a diluent solution. The diluent solution may include any suitable biocompatible solution as understood in the art including for example, sterile saline solution, sterile isotonic saline, sterile phosphate-buffered saline, and the like.

The injectable scaffolds, including one or more microfibers as described herein and one or more diluent solutions, can be crosslinked once injected into a site or region of interest such as a tissue defect. The one or more injected scaffolds can be crosslinking using one or techniques as understood in the art. For example, the microfibers can include photo-crosslinkable groups including, but not limited to, methacrylate and acrylate groups. In such embodiments, the microfibers crosslink when exposed to light including visible light, UV light, and the like.

In certain embodiments, the injectable scaffolds are crosslinked by a surface protein crosslinkable by an enzyme. For example, the microfibers can include one or more pairs of surface proteins and enzymes including fibrinogen vs. thrombin, such that when the protein and enzyme pair come in contact with one another, crosslinking occurs between the one or more microfibers in the injectable scaffold.

In certain embodiments, the injectable scaffolds are crosslinked by the reaction between two types of surface chemical groups. For example, the microfibers can include one or more pairs of surface chemical groups including, but not limited to, thiol vs. maleimide groups, azide vs. alkyne groups, alkyne vs. nitrone groups, alkene vs. tetrazine groups, biotin vs. streptavidin groups, and n-hydroxysuccinimide vs. amine groups such that when the microfibers having opposing surface chemical groups come in proximity, the microfibers crosslink.

Methods

Embodiments of the present invention provide one or more methods 1300 for repairing a soft tissue defect in a subject. The subject is a mammal, including a human. The tissue defect can include a tear such as a partial tear, a full tear, or other defect as understood in the art.

Figure 13:
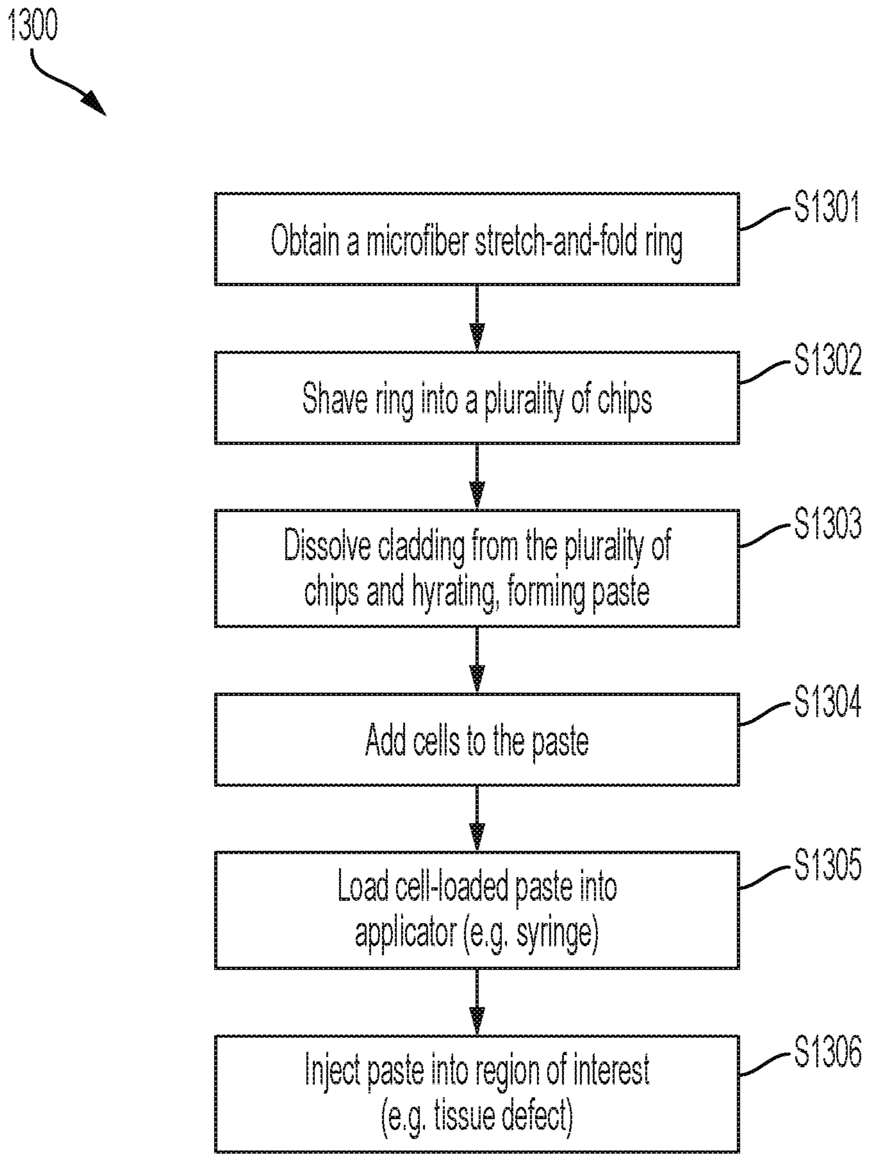
FIG. 13 depicts an exemplary method of repairing a defect in a tissue according to an embodiment of the present invention.

Referring now to FIG. 13, embodiments of step S1301 of method 1300 includes obtaining a microfiber stretch-and-fold ring comprising a microfiber and a cladding. In certain embodiments, the microfibers stretch-and-fold ring is fabricated according to an exemplary stretch-and-fold method such as that described in U.S. patent application Ser. No. 15/816,639, which is incorporated herein by reference in its entirety. The cladding can include any suitable cladding polymer as understood in the art including, for example, polycaprolactone (PCL), polylactic acid (PLLA), polyglycolic acid (PGA), polystyrene (PS), poly, polyvinyl chloride (PVC), polybenzimidazole (PBI), polyetherether ketone (PEEK), polyoxymethylene (POM), polyetherimide (PEI), polyethylene (PE), polyphenylene oxide (PPO), polypropylene (PP), polyphenylene sulfide (PPS), polyvinylidene fluoride (PVDF), and the like, including combinations thereof.

The microfiber can be constructed from one or more suitable natural or synthetic polymer as understood in the art. For example, the one or more natural polymers can include one or more of gelatin, collagen, elastin, hyaluronic acid, chondroitin sulfate, dextran, silk protein, chitosan, alginate, heparin, heparin sulfate, and laminin. The one or more synthetic polymers can include one or more of polyethylene glycol, polycaprolactone, polylactic acid, polyglycolic acid, polylactic-glycolic acid, Teflon™, Nylon™, polycarbonate, polyamide, polystyrene, polypropylene, and polyester.

Embodiments of step S1302 of method 1300 include shaving the stretch-and-fold ring into a plurality of chips. The chips comprise a thickness of about 200 μm. The chips comprise a length of from about 200 μm to about 5000 μm.

Embodiments of step S1303 include dissolving or uncladding the plurality of chips with an uncladding solution and/or solvent in order to unclad the microfibers. The uncladding solution or solvent can include any suitable solvent including any organic solvent suitable for dissolving the cladding polymer. For example, the uncladding solution/solvent can include acetone, chloroform, hexane, ethanol, methanol, pentane, methylcyclohexane, ethane, dimethyl sulfoxide, ethyl ether, perfluoropentane, perfluoromethylcyclohexane, hexafluoroethane, perfluoro-1,3-dimethylcyclohexane, perfluoromethyldecalin, and the like. In some embodiments, the unclad microfibers are further hydrated using hydrating solution, thereby forming a paste. The hydrating solution can include one or more of PBS, cell culture media, saline, sterile water, or another suitable injectable solution Embodiments of step S1304 include introducing a plurality of cells into the paste, thereby forming a seeded paste. The plurality of cells can include one or more chondrocytes, pluripotent cells, stem cells, fibroblasts, etc. The cells can include any suitable cell as described herein including, for example, embryonic cells, neonatal cells, autograft cells, allograft cells, xenograft cells, and the like.

Embodiments of step S1305 include loading the cell-seeded paste into an applicator including, for example a syringe. The applicator can be loaded with a volume suitable for filling the defect in the region of interest. For example a volume including up to about 1 mL, about 1 mL to about 5 mL, about 5 mL to about 10 mL, about 10 mL to about 20 mL, about 20 mL to about 30 mL, about 30 mL to about 40 mL, about 40 mL to about 50 mL, about 50 mL to about 60 mL about 60 mL to about 70 mL, about 70 mL to about 80 mL, about 80 mL to about 90 mL, about 90 mL to about 100 mL, and so on. In some embodiments, 25 mL is injected.

Embodiments of step S1306 include injecting the seeded paste into a region of interest. The region of interest can include one or more regions including one or more load-bearing tissues such as bone and/or cartilage. The paste can be injected using, any suitable applicator as understood in the art including for example one or more minimally invasive applicators such as arthroscopy needles, one or more syringes and needles, and the like. The one or more syringes and needles can include a 22 g needle or larger. The seeded paste can be injected to fill a random defect with arbitrary geometry before forming a scaffold.

Embodiments of method 1300 can further include crosslinking the seeded paste. The seeded paste can be crosslinked using any suitable means as understood in the art, and as described elsewhere herein, including for example, applying visible light, UV light, glutaraldehyde, BDDE, etc.

Kits

Embodiments of the present invention provide one or more kits comprising at least one injectable scaffold of the invention, a plurality of cells in solution, an applicator and an instructional material for use thereof.

The plurality of cells includes a plurality of any type of adult cells or precursor cells such as for example, chondrocytes, fibroblasts, stem cells, pluripotent cells, progenitor cells. The solution includes any suitable solution such as sterile cell culture media, sterile saline, and the like.

The applicator can include a sterile syringe and needle. The needle is sized in order to effectively deliver the at least one injectable scaffold and plurality of cells in solution to a site of interest in a subject. For example, the needle can include a 22 gauge needle. Embodiments of the kits can include one or more of a 12 gauge needle, a 16 gauge needle, an 18 gauge needle, 20 gauge needle, a 22 gauge needle, a 24 gauge needle, and the like.

Embodiments of the kit include means for crosslinking the injectable substrate, including for example one or more light sources including one or more UV light sources, one or more solutions including glutaraldehyde, 1,4-butanediol diglycidyl ether (BDDE), fibrin glue, click chemistry functional groups incorporated into the at least one injectable scaffolds, and the like.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and use the compounds of the present invention and practice the claimed methods. The following working examples therefore, specifically point out the preferred embodiments of the present invention, and are not to be construed as limiting in any way the remainder of the disclosure.

Micro/nanofibers have gained great popularity as a biomaterial for tissue engineering. For healing muscles, nerves and tendon tissue, for example, aligned micro- and nanofibers may provide the biophysical cues for guiding cell alignment and tissue growth. On the other hand, non-aligned fibers can provide a highly porous space for cell spreading, migration and proliferation in 3D, which promotes the regeneration of bones, cartilage and fat tissues. However, current approaches to fabricate micro- and nanofibers, such as electrospinning, thermal spinning and wet spinning, are often limited due to the difficulty in controlling fiber diameter, small variety of suitable materials, long fabrication time, and low production rate. Furthermore, it is difficult to create micro- and nanofibers using hydrogels, which are major biomaterials for regenerative medicine. To overcome these limitations, a novel method to mass-produce micro- and nanofibers using stretching and folding has been developed. This technique is designed for creating micro- and nanofibers by a clinical-relevant quantity and is especially suitable for making hydrogel-based fibers.

Example 1. Synthesis of Subcellular Scale Microfibers from Gelatin

Soft tissues injuries and degeneration is a serious health problem in the world. In the USA, intervertebral disk degeneration affects approximately 30 million people every year. Osteoarthritis affects more than 27 million people and is predicted to affect 1 in 2 individuals in their lifetime. Treatments for these diseases command a large percentage of the total overall health care budget in the US. Surgical interventions are needed to restore soft tissues integrity and prevent further tissues deterioration.

Methods

In an embodiment of the stretch-and-fold method, a ring-shaped precursor made of porcine gelatin (for core) and polycaprolactone (PCL) (for sheath) was created, and using the stretch-and-fold procedure, the precursor was turned into gelatin micro and nanofibers (FIG. 5). The diameter of core gelatin fibers was tuned from about 100 microns to below 100 nanometers by increasing the number of stretch-and-fold cycles from 10 to 28, and the core fibers were released by dissolving the PCL sheath. The stretch-and-fold procedures reduces the diameter of the core fibers exponentially, therefore the production rate of micro and nanofibers is extremely higher than any of the existing manufacturing methods. Such production rate is not determined the quantity of material; a larger yield can be achieved by starting the stretch-and-fold procedure with a larger precursor ring. Following are the corresponding experimental details.

Prepare Gelatin Solution

To prepare the gelatin for microfiber fabrication, gelatin from porcine skin (Sigma-Aldrich, Cat #1890) was dissolved in pure water at 50 wt % and stirred at 100 rpm on a hot plate at 70° C. After the gelatin powder was fully dissolved, the gelatin solution was centrifuged at 50° C. for 10 minutes to remove air bubbles.

Encapsulating Gelatin PCL Ring and the Stretch-and-Fold Procedures

A ring-shaped precursor is prepared as follows. Polycaprolactone (PCL) pellets (50 g) were melted in a bath of olive oil at 75° C. After becoming transparent and plastic, the clump of PCL was removed from the oil bath and molded into a tube with 5 mm internal diameter (ID) and 20 mm external diameter (OD). The PCL tube became opaque and solidified after cooling by air at room temperature. The gelatin solution obtained in the previous step was injected into the PCL tube using a 25 mL syringe. The ends of the PCL tube were sealed by melting PCL to contain the gelatin solution.

Figures 5A, 5B, 5C, 5D:
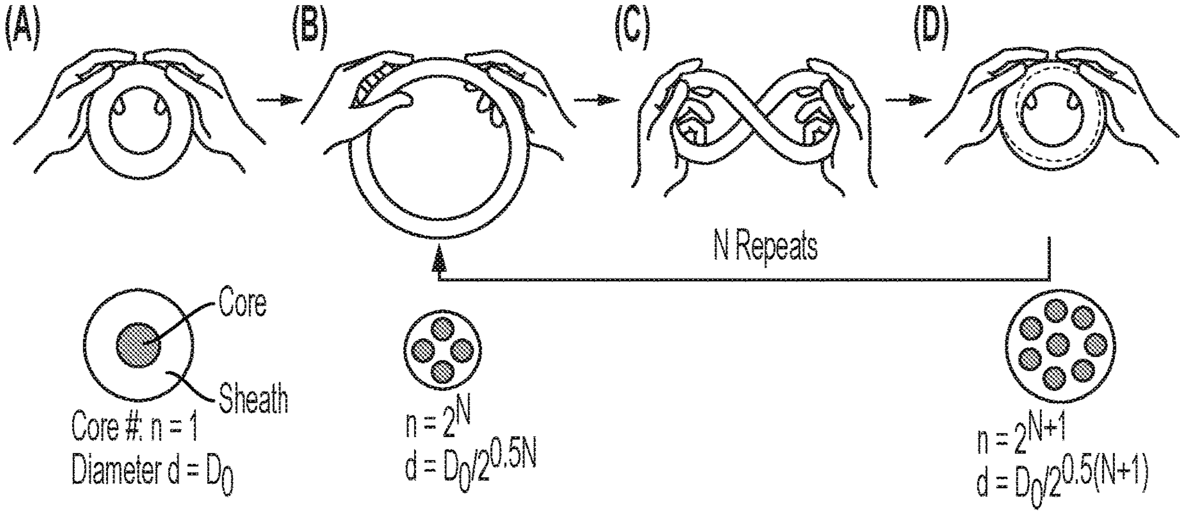
FIGS. 5A-5D depict an additional "Stretch-and-Fold" embodiment as contemplated by the present invention.

To conduct stretch-and-fold procedures, the PCL tube, now with a core of gelatin, was heated in a 75° C. water bath with constant rolling. Upon exceeding the glass transition temperature of PCL (>60° C.), the PCL tube became plastic and accessible to stretching and folding. To form a PCL ring, the ends of the PCL tube were joined together, as shown in FIG. 5A. Immediately after this step, the ring was repeatedly stretched and folded (FIGS. 5B, 5C and 5D) in order to thin (reduce the diameter of) the gelatin cores, until the desired core diameter is reached. The stretch-and-fold procedure was conducted swiftly in the ambient air before the PCL solidified. The folded PCL ring was immediately cooled and solidified at room temperature.

Chopping the Stretched and Folded Ring into Thin Segments

A unit feature of Injectable scaffold is the injectability. Such injectability relies on a proper control of microfibers length. If the microfibers are too long, the friction between microfibers makes injecting with a needle nearly impossible. On the other hand, if the microfibers are too short, the contacts between fibers become insufficient, which renders the crosslinking of microfibers difficult and weakens the scaffold. An ideal microfiber length was found to be:

(a) Below the inner diameter of the needle by which the injectable scaffold is injected, such that individual fibers may pass the needle easily; and (b) Significantly longer than the gap space between fibers, such that there may be sufficient contacts between the fibers.

Figure 6:
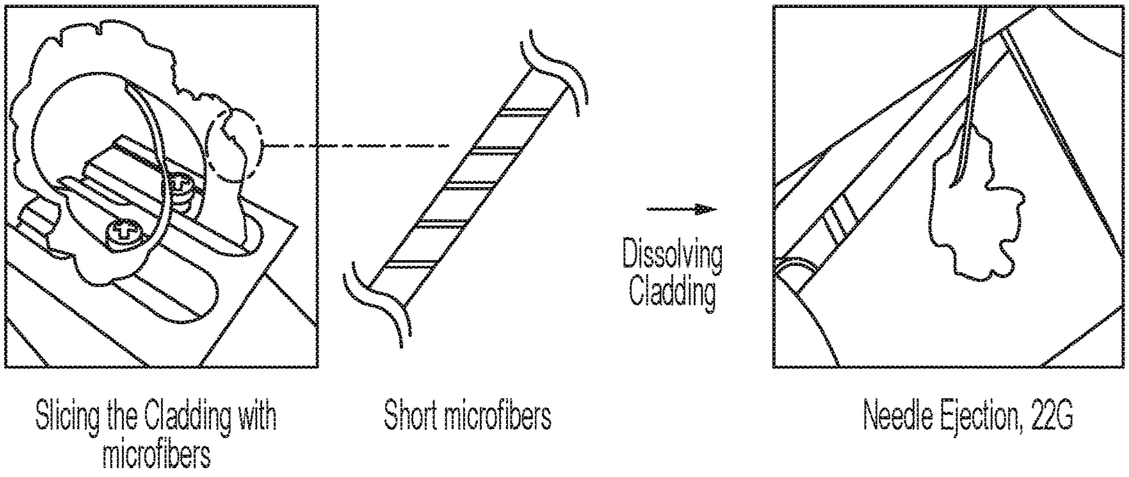
FIG. 6 depicts an exemplary method of shaving the microfiber ring. Using a pencil-sharpener, the stretched-and-folded ring are pealed into thin slides that are about 200 μm thick, in which the microfibers are about 200 μm long. Microfibers of this length form a paste that can be delivered through a 22 gauge needle which is thinner than standard epidural needles (20 gauge).

To control the fiber length, after the stretch-and-fold procedures and before the dissolving of the cladding material, a slicing equipment was used to chop the stretched-and-folded ring laterally into thin slices. In this way, the length of each microfibers equals the thickness of the slides. The slicing equipment can be any machine that is capable of slicing a bulk material into slices of constant thickness. Specifically, it can be a histology microtome or even a meat slicer. Preliminary products were prepared using a pencil-sharpener to peal the stretched-and-folded ring into thin slices that were about 200 μm thick, in which the microfibers became about 200 μm long (FIG. 6). This enabled the microfibers of the injectable scaffold to be delivered by a thin needle. The thickest needles used to successfully deliver injectable scaffold were 22 gauge needles, which are thinner than the standard epidural needles for spinal injection (which are 20 gauge).

Retrieving gelatin micro nanofibers from PCL To retrieve micro/nanofibers, the stretched-and-folded PCL ring was chopped into thin segments and dissolved by acetone at 30° C. under mild agitation, which released the gelatin core fibers. As-retrieved fibers were rinsed by fresh acetone at 30° C. for five times to remove PCL residue (30 minutes each time). The resulting fibers was fixed in glutaraldehyde solution (0.1% in methanol) for three hours, neutralized in lysine solution (1% in methanol), dialyzed against distilled water for 3 days, and finally freeze-dried for storage. The diameter of core fibers was adjustable by the number of stretch-and-fold cycles, and can be tuned from hundreds of micron down to sub-micron, following a simple equation: Dn=D0/20.5n, where n the number of stretch-and-fold cycles, D0 is the original core diameter before folding, and Dn is the core diameter after n stretch-and-fold cycles.

Alternative to Injectable Scaffold: Making Long Microfibers that are Aligned

Figure 7A:
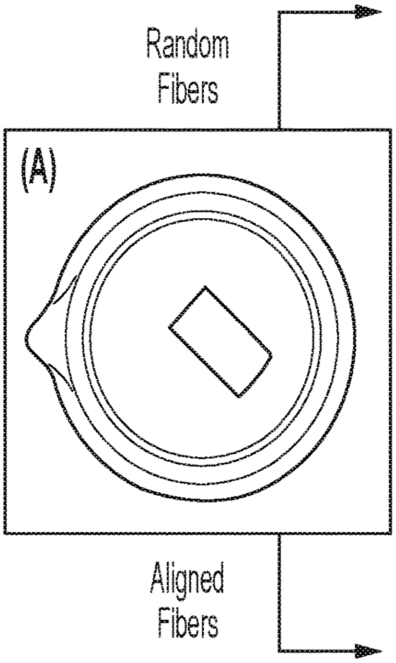
FIGS. 7A-7E depict the retrieval of porcine gelatin microfibers (5 μm diameter) from a segment of PCL ring, shown in FIG. 7A. Dissolving of the PCL cladding and releasing the core fibers is shown in FIG. 7B. The diameter of core fibers is determined by the number of stretch-and-fold cycles and is tunable from sub-micron to hundreds of microns, shown in FIG. 7C. Pre-aligned fibers (FIG. 7E) are obtained by restraining the ends of the ring segment during PCL dissolving (FIG. 7D).
Figure 7B:
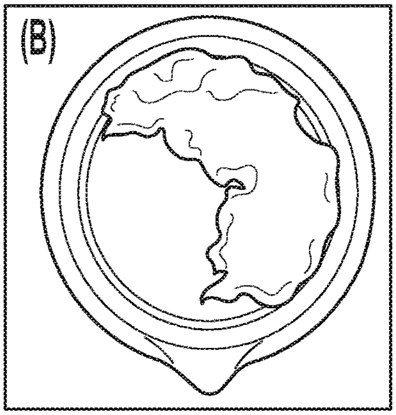

One of the major advantages of the stretch-and-fold method is the ease to obtain aligned fibers, since the PCL sheath maintain the linear organization of core fibers throughout stretching and folding. In contrast to injectable scaffolds with short and random microfibers, aligned microfibers are not injectable by needles but can be used to engineer long and linear tissues, such as tendons and muscles. To maintain the micro/nanofibers alignment, the stretched-and-folded rings were cut into long segments (>5 cm). Clips were used to constrain the core fibers at the ends of the segments (FIG. 7D), before following through the above protocols. This method produces a bundle of aligned micro/nanofibers (FIG. 7E). Randomized the microfibers during dissolving led to random fiber organization (FIG. 7A to 7C).

Figure 7C:
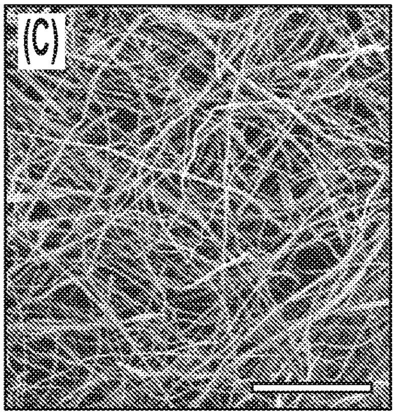
Figure 7D:
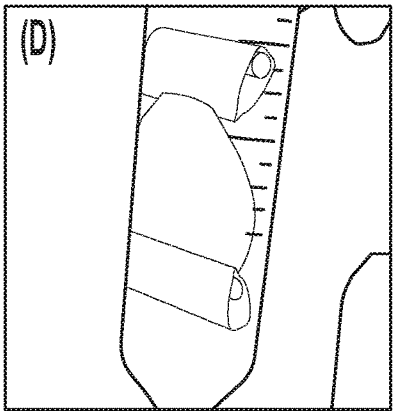
Figure 7E:
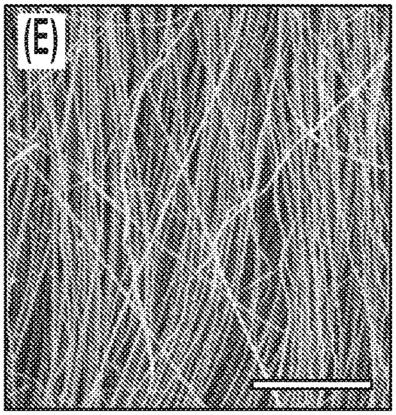

Scaffolds made with the aligned and random fibers have controlled pore or channel size that is roughly five to ten times of the diameter of the individual microfibers (FIGS. 7C and 7E). The pore size was been found to impact the differentiation of stem cells. Smaller pores that induce rough cell morphology were found to promote chondrocyte-like cell phenotypes (which is suitable for cartilage repair) and nucleus pulposus-like cell phenotypes (which is suitable for IVD repair). Larger pores, on the other hand, promote cell spreading and induce fibrous tissue-like cell phenotypes (which is more suitable for tendon repair).

Tuning Fiber Elasticity

Besides pore size, elasticity is another important factor to the efficiency of cartilage repair. For tissue fillers and wound dressers, the elasticity of micro/nanofibers determines the biophysical signals that cells sense from the product, which in turn affects the pace of wound healing and the formation of different tissue types through cell-mechanosensing. Matrices softer than 1 kPa in Young's modulus were shown to promote fat tissue formation, as matrices harder than 50 kPa shown to promote bone formation. Elasticity of fibers produced by stretching-and-folding is determined by the crosslinking of core compartment. Fiber crosslinking was achieved by using glutaraldehyde (0.1% in methanol, 3 hours), which crosslinks porcine gelatin rapidly by binding lysine croups. The elasticity given by glutaraldehyde treatment can be tuned from 0.1 kPa to 20 kPa, as higher glutaraldehyde concentration and longer treatment produce higher elasticity. To enhance the mechanical property of fibers, glutaraldehyde can be replaced or added with other crosslinking chemical, such as 1,4-butanediol diglycidyl ether and methacrylate.

In comparison with glutaraldehyde, 1,4-butanediol diglycidyl ether (BDDE) is a slower crosslinker, but the slower reaction enables more uniform BDDE diffusion and enhances the mechanical homogeneity of fibers. The following steps are added to the protocols described herein if BDDE is used instead of glutaraldehyde:

a) Add 0.01% to 1% BDDE to the gelatin solution, which crosslinks gelatin via lysine function groups. Glycidol at higher concentration leads to higher Young's Modulus.
b) Omit the use of glutaraldehyde.
c) Before retrieving the core fibers from PCL, treat the as-folded PCL ring in 50% oil bath for 24 hours. The heating accelerates glycidol-crosslinking.

Methacrylate groups form the stiffest matrix in comparison with glutaraldehyde and BDDE and can significantly increase the range of Young's Modulus. The following steps are added for methacrylate-based crosslinking:

a) After retrieving the core fibers from PCL, rinse the fibers in methanol with 1% to 20% methacrylate anhydride for 30 minutes at room temperature. This introduces methacrylate groups to gelatin via lysine groups.
b) Use glutaraldehyde as described herein.
c) Crosslink methacrylate groups before freeze-drying: rinse the fibers in water containing 0.05% phenyl-2,4,6-trimethylbenzoyl-phosphinate (LAP), expose the fibers to ultraviolet light (4 mW/cm$^2$) for 10 minutes, then wash the fibers twice by distilled water. Methacrylate crosslinking leads to a final Young's Modulus of 1 kPa to 100 kPa, which is tunable by changing the concentration of methacrylate anhydride in (1).

Independent Control of Fiber Elasticity and Diameter

Since elasticity and diameter are both important to the performance of micro/nanofibers, decoupled and independent control of these parameters would be highly desirable to the manufacturers. To verify whether fiber diameter and elasticity can be independently tuned, microfibers produced with different diameters (via different stretch-and-fold cycles) but the constant crosslinking density (with BDDE) were prepared following the above protocol. The fiber diameter was measured by using SEM, and the fiber elasticity was measured by nanoindentation based on atomic force microscope (AFM).

Nanoindentation was carried out via a Dimension Icon AFM (BrukerNano, Santa Barbra, CA) under physiological-like conditions (PBS, ionic strength≈0.15 M, pH 7.4, indentation rate≈10 μm/s). Custom-made borosilicate micro-spherical tips with radii comparable to the size of as-manufactured fibers (nominal spring constant k≈0.2 N/m) was used to simulate the micromechanical force that living cells sense. At each indentation location, the force versus depth (F-D) curves was quantified through the established calibration procedures. In the meantime, contact mode imaging was performed with the same tip under minimized compressive force (about 1 nN) to quantify the fibers 3D topography, i.e. thickness t, following the existing protocol. Effective indentation modulus, Eina, was calculated by applying linear elastic Hertz model to the loading portion of each F-D curve. Substrate constraint effects due to finite thickness t was corrected by:

$$F=\left(4*E_{ind}*R^{\frac{1}{2}}*D^{\frac{3}{2}}\chi\right)\div\left[3\left(1-v_{p2}\right)\right]$$

where $v_P$ is the Poisson's ratio (≈0.49 for highly swollen hydrogels), and $\chi$ the substrate constraint correction factor (negligible when thickness>10×maximum of D). In all measurement, the maximum indentation depth, $D_{max}$, was made <500 nm (<20% local strain) to minimize material mechanical nonlinearity. At $D_{max}$, the maximum tip-sample contact radius is ≈2 μm, and thus, spatial maps of $E_{ind}$ was obtained at this resolution of ≈2 μm through controlling the close-looped X-Y piezo-stage of the AFM.

Figure 8:
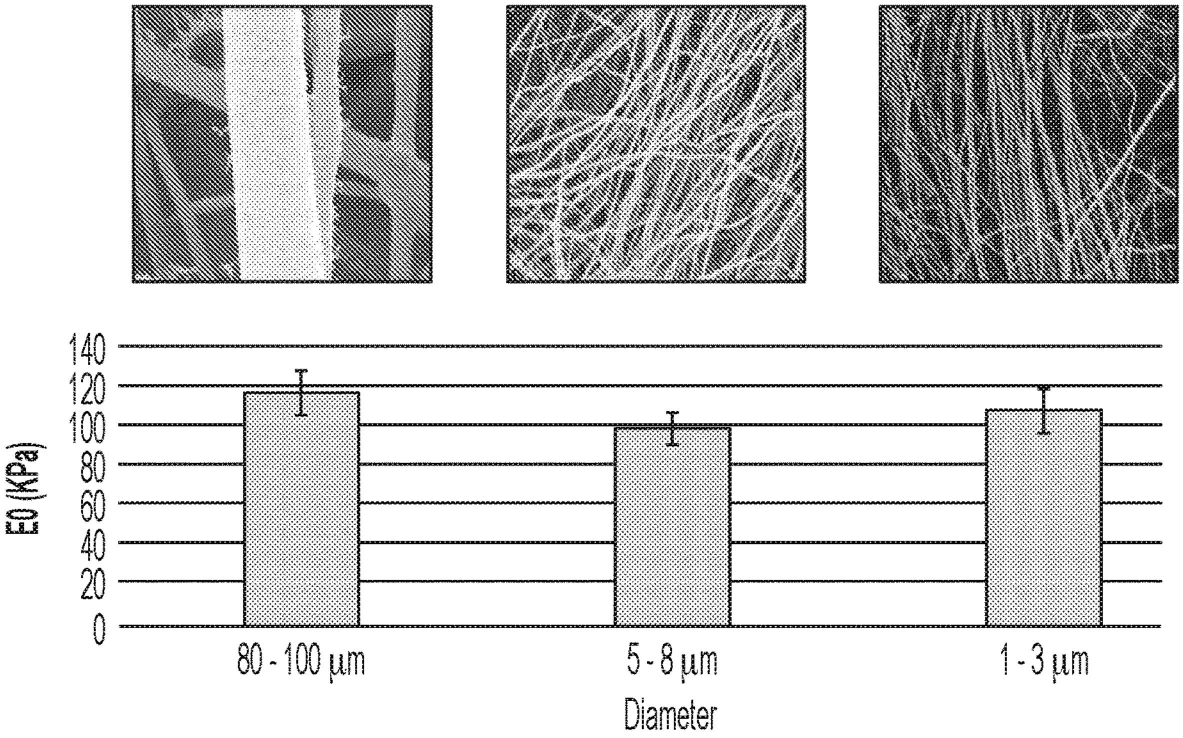
FIG. 8 demonstrates that the fibers have both decoupled and independently controllable elasticity and diameter. The elasticity measurements are conducted by nanoindentation with AFM. The fibers are made of gelatin crosslinked by BDDE. The elasticity is controlled independently by the concentration of BDDE, while the diameter is tuned by the number of stretch-and-fold cycles.

The results from nanoindentation showed that the fiber elasticity was consistently 110±10 kPa regardless of varying fiber diameter (FIG. 8). This result verifies that the stiffness and diameter of stretched-and-folded fibers can be independently controlled by the crosslinking density of the core compartment and the number of stretch-and-fold, respectively.

Example 2: Mouse Cranial Defect Model

Introduction

Adipose derived stromal cells (ADSCs) represent a promising source of autologous stem cells for tissue repair given their relative abundance and potential to differentiate towards bone lineage. For repairing large defects, scaffolds with macropores are highly desirable to promote nutrient diffusion, fast blood vessel in growth, and new tissue formation. Various methods have been developed for fabricating macroporous scaffolds including particle-leaching, phase separation, gas foaming and electrospinning. However, these methods require the use of non-physiological conditions and are not cell-friendly. As a result, cells can only be seeded onto the scaffolds post-fabrication, which makes it very difficult to achieve homogeneous cell seeding in scaffolds for repairing large bony defects. To overcome this limitation, development of microfiber-like, crosslinkable elastomers as scaffold building blocks is reported herein, which support direction cell-encapsulation while simultaneously forming macroporous scaffolds. The goal of this study is to evaluate the potential of microfibers based, macroporous scaffolds for repairing tissue defects in vivo using a mouse critical size cranial defect model.

Methods

Methacrylated gelatin (GelMA) was prepared by existing protocol. Crosslinkable, gelatin-based microfibers were synthesized. Passage 2 mouse ADSCs isolated from GFP-Luciferase positive mice were used for the study. For cell encapsulation, mADSCs were mixed with either crosslinkable microfibers or GelMA (10% in PBS) to reach a concentration of 10 M/ml, and photocrosslinked into cell laden cell scaffolds (365 nm, 2 mW/cm$^2$, 4 min). Acellular scaffolds were included as controls. Critical size cranial defect (4 mm) was made in athymic mice in the parietal bones as previously reported. Four groups were tested including fiber-based scaffold with mADSCs, hydrogel-based scaffold with mADSCs, and both types of scaffolds without cells. Mice with empty defects were used for negative control. From day 0 to week 6, cell viability and location of implants were monitored weekly via bioluminescence imaging (BLI). At 0, 2, 4, and 6 weeks, the mineralization of the implants was monitor by micro computed tomography (CT) scanning. Animals were sacrificed on day 3 and at week 6 and tissues are harvested for histology.

Results

Figure 9A:
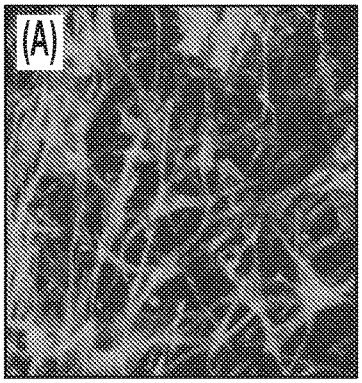
FIGS. 9A-9C demonstrate that fiber-based scaffolds (FIG. 9A) but not hydrogels (FIG. 9B), induced extensive cell spreading 24 hours post-encapsulation.
Figure 9B:
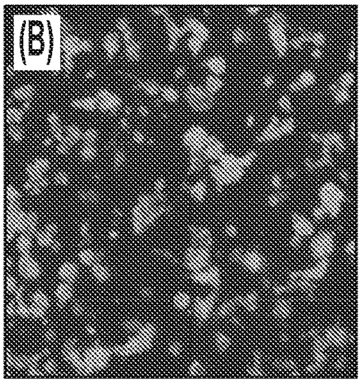
Figure 9C:
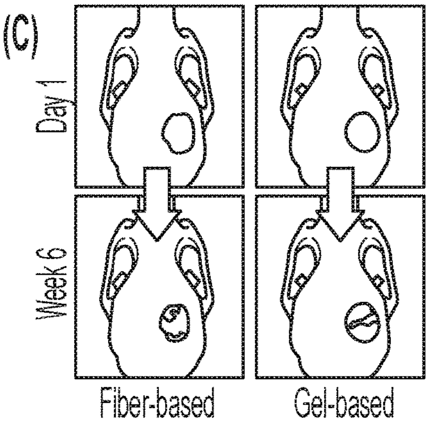

Confocal imaging showed extensive cell adhesion and spreading of mADSCs throughout 3D fiber-based scaffolds 24 hours post cell seeding (FIG. 9A). In contrast, cells in hydrogels remained round morphology with minimal cell spreading (FIG. 9B). By week 6, fiber-based scaffolds also resulted in twice as many ADSCs in comparison with the HG-based implants by week 6, as shown by bioluminescence imaging. Histological staining of CD31 showed higher blood vessel density inside fiber-based scaffolds vs. hydrogel scaffolds. MicroCT imaging results demonstrated that fiber-based scaffolds accelerated bone regeneration with almost complete filling of the defects, yet minimal bone repair was observed in the hydrogel group (FIG. 9C). The acellular control groups showed negligible bone regeneration, with less than 6% of bone volume refilled. Histology also showed the highest level of collagen deposition in the fibers-ADSC group.

Example 3. In Vitro Cartilage Formation

Introduction

To verify the potential of nano/micro-fibers of the invention for tissue engineering, human mesenchymal stem cells (hMSCs) were encapsulated in hand-spun microfibers (2 μm in diameter) for chondrogenesis study. Results showed uniform cell distribution, cartilage-like extracellular matrix (ECM) formation, and significantly increased mechanical property in the microfiber-based scaffolds.

Methods

Figure 10A:
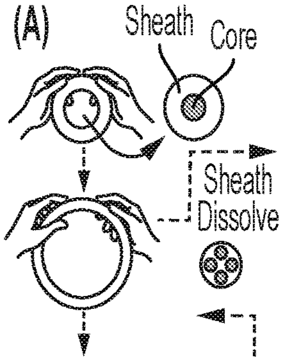
FIGS. 10A-10J illustrate micro/nanoscale c-fiber preparation.
Figure 10C:
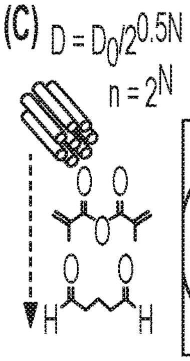
Figure 10E:
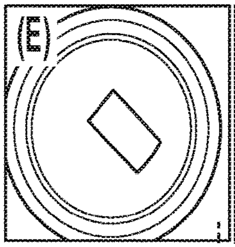
Figure 10G:
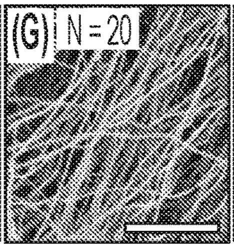
Figure 10I:
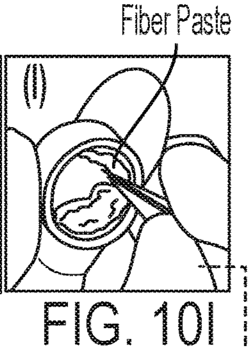
Figure 10B:
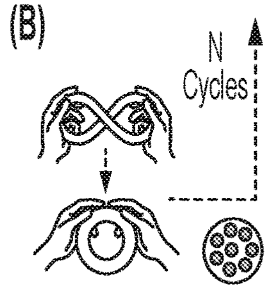
Figure 10D:
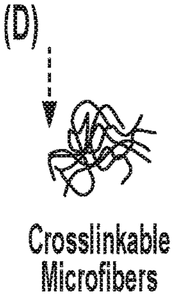
Figure 10F:
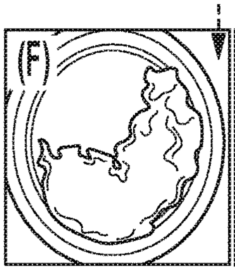
Figure 10H:
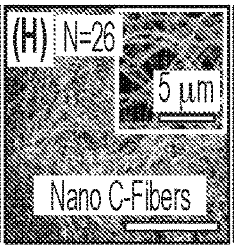

The stretch-and-fold method is used to produce micro/nanoscale, crosslinkable fibers (C-fibers) with a widely tunable diameter. A precursor ring was repeatedly folded and stretched that contained both a core and a sheath compartment (FIGS. 10A to 10F). The core contained hydrated gelatin, and the sheath was made of a solvent-soluble polymer that kept the cores separated. The stretch-and-fold cycles (n) increased the cores number (N) exponentially (N=2n) while decreasing the core diameter exponentially ($D=D0/2^{0.5n}$) (FIGS. 10G to 10J). Twenty-six stretch-and-folding cycles, for example, turns a 2 mm gelatin core into 67,108,864 parallel fibers and having a 250 nm average diameter (FIG. 10H). C-fibers were retrieved by acetone leaching, aldehyde-fixed, methacrylated, dialyzed and freeze-dried for storage.

Experiment I

The effect of large macropores was examined. Cellularized scaffolds containing 100 μm to 200 μm-sized pores were prepared by encapsulating human mesenchymal stem cells (MSC) (20 M/cm$^3$ density) by 50 μm-wide C-fibers (7.5 wt %) (FIG. 10E). To examine the effects of porosity, a control group was prepared by encapsulating MSC in hydrogels made of methacrylated gelatin, which formed 1 μm to 2 μm-sized pores that were much smaller than MSC (about 15 μm) (FIG. 10F). Scaffolds were cultured with chondrogenic medium under 37° C. and 5% $CO_2$. Samples were collected on day 1 and day 21 for analysis.

Experiment II

Next, the effect of intermediate pore size was examined by repeating Experiment I using 4 μm and 25 μm C-fibers (prepared by 14 vs. 20 stretch-and-fold cycles), which formed μm to 20 μm and 100 μm to 200 μm pores, respectively. In Experiment II, the cell density was reduced from 20 to 5 or 10 million/cm$^3$, in order to minimize the effect of cell-cell contacts, which is known to promote chondrogenesis via the activation of HIPPO signaling. All groups were repeated at least in triplicate (n>3).

Results

Macropores Facilitate ECM Formation

Figure 10J:
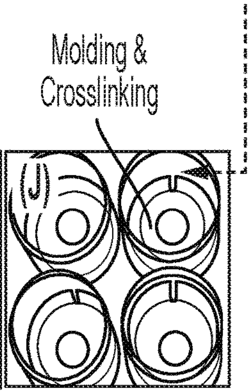
Figure 11A:
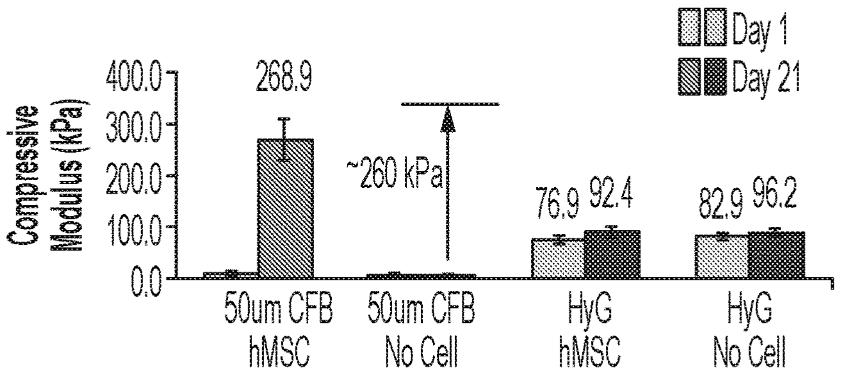
FIGS. 11A-11Q demonstrate results verifying the effects of matrix porosity on chondrogenesis. Scale bar in FIGS. 11E, 11F, 11M, and 11N is 100 μm. The staining in FIGS. 11K and 11L is as follows: blue, cell nuclei; green, microtubules; red, actin filaments.
Figure 11B:
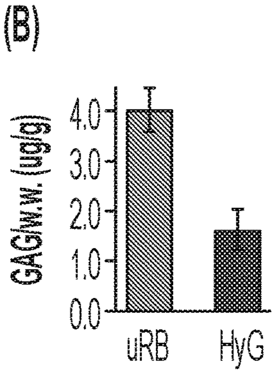

The 100 μm to 200 μm pore samples exhibited dramatically increased compressive moduli (Δ≈260 kPa) on Day 21 vs. Day 1, while the 1 μm to 2 μm pore samples had only slightly increased moduli (Δ≈15 kPa) (FIG. 11A). DNA and biochemical analyses showed twice as many cells per gram and 2.5-times as much glycosaminoglycan (GAG) per gram in the C-fiber scaffolds in comparison with the hydrogels (FIG. 11B). Examination of the spatial distribution of GAG, aggrecan (Agg) and type-II collagen (Col-II) on the Day-21 scaffolds showed that these ECM components formed interconnected networks through the 100 μm to 200 μm pore samples (FIG. 11G, 11I), but formed only pericellular precipitates in the 1 μm to 2 μm pore samples (FIG. 10H,10J). Material mechanics theory reveals that the observed morphology of ECM was responsible for the dramatic difference in bulk stiffening, as Col II and GAG may dominate the bulk stiffness by extending across the bulk volume.

Cell Morphology Affects Stem Cell Phenotype.

Figure 11C:
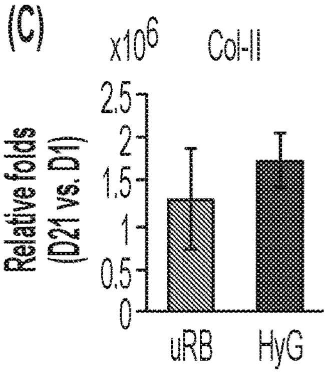
Figure 11D:
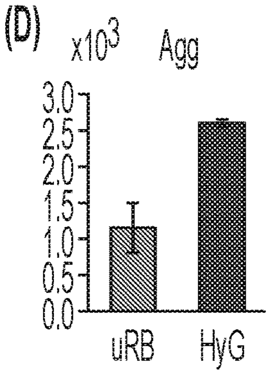
Figures 11E, 11G, 11I, 11K:
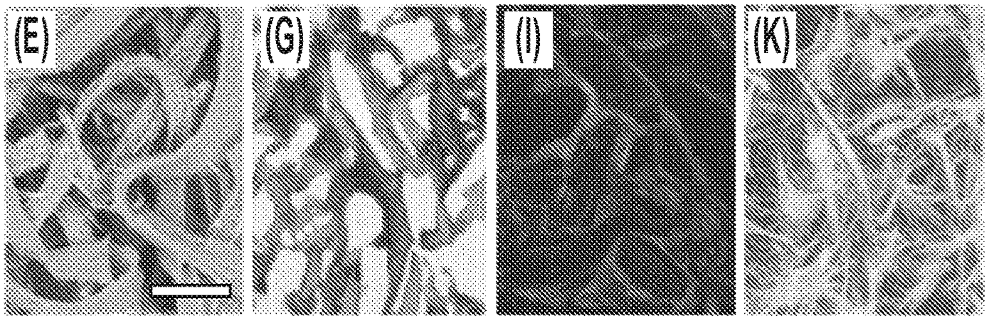
Figures 11F, 11H, 11J, 11L:
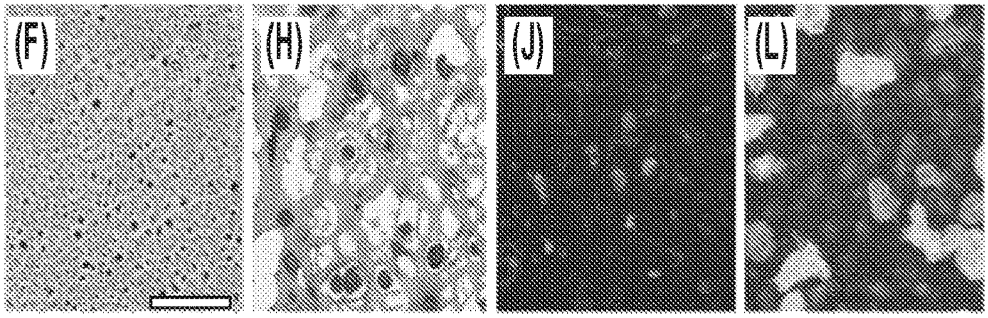
Figures 11M, 11N:
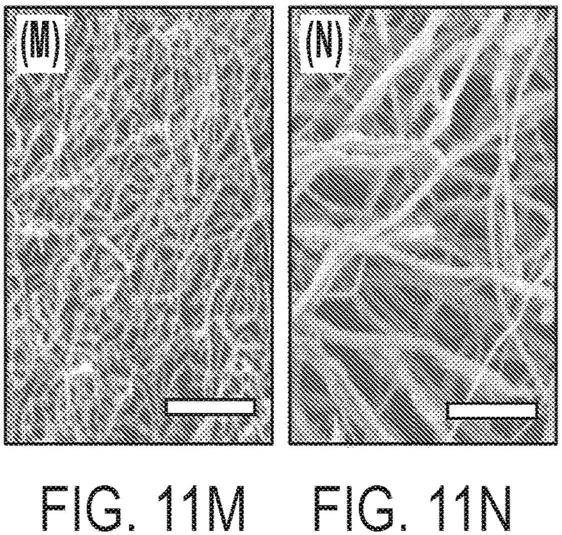
Figure 11O:
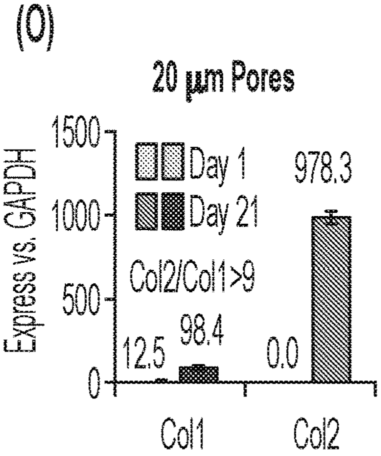
Figure 11P:
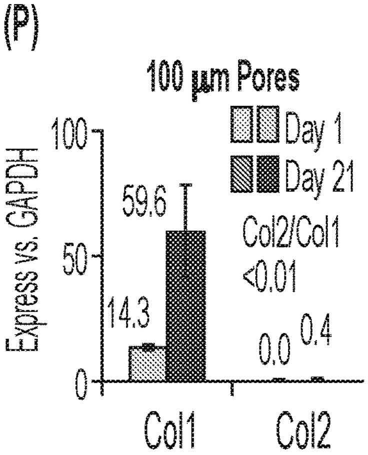
Figure 11Q:
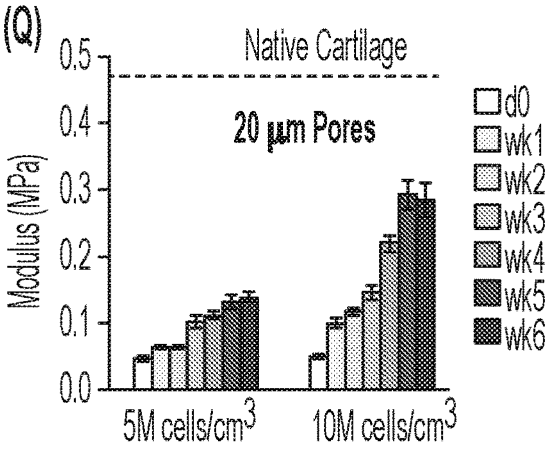
Figure 12A:
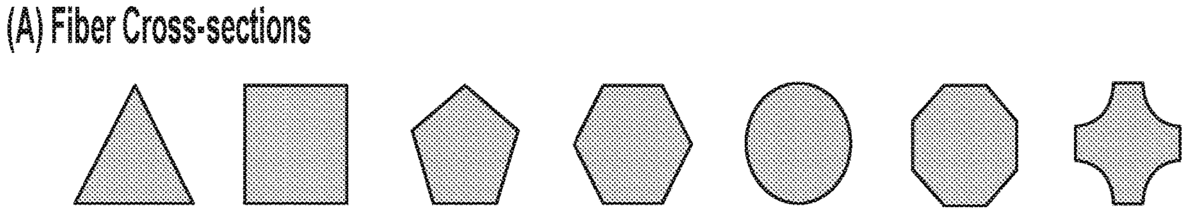
FIGS. 12A and 12B depicts exemplary cross-sections of microfibers as contemplated herein. The microfibers in the injectable scaffold can have alternative compositions: Panel A depicts different cross-sections, and Panel B depicts cross-sections with compartments.
Figure 12B:
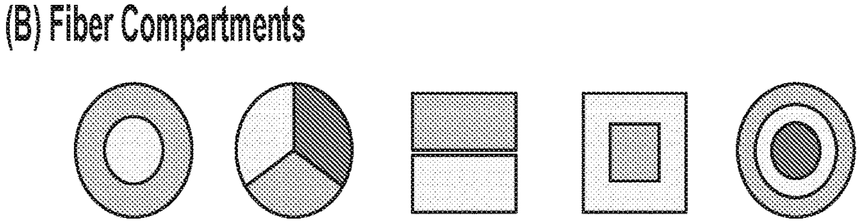

The 100 μm to 200 μm pores led to spreading cell morphology resembling fibroblasts (FIG. 11K). In contrast, the 1 μm to 2 μm pores resulted in round cell morphology (FIG. 11L). Despite the supportive effects of macropores on matrix formation, real-time PCR analysis on the day-21 samples showed decreased hyaline cartilage markers expression, including GAG, Col-II and Agg, in the macroporous-cultured MSCs in comparison with the hydrogel-cultured MSCs (FIG. 11C to 11D). The correlation between the above results suggests that round MSC morphology promoted hyaline cartilage phenotype. Intermediate pore size better supports chondrogenesis. At low cell density (5 M/cm$^3$), MSC in the 10 μm to 20 μm pores scaffolds showed dramatically higher Col-II/Col-I expression ratio (about 10) in comparison with cells in the 100 μm to 200 μm pores scaffolds (Col-II/Col-I<0.01), showing that 10 μm to 20 μm, or cell-sized pores promote chondrocyte phenotype (Col-II/Col-I>>1), and that 100 μm to 200 μm pores promote fibroblast- or fibrochondrocyte-like phenotype (Col-II/Col-I<<1) (FIG. 11M to 11P). The samples with 10 μm to 20 μm pores continued to stiffen for 6 weeks and exceeded 30% natural cartilage strength (about 450 kPa) Increasing cell density from 5 to 10 M/cm$^3$ accelerated stiffening and led to 65% natural cartilage strength by week 6 (FIG. 11Q).

Example 4. Horse Model Studies

Introduction

Horse model is considered one of the most clinically relevant animal models to test cartilage implants. Cartilages from the horse stifle joints resemble human knee cartilage in many aspects, including the stiffness, average thickness (~2.5 mm) and mechanical stresses they sustain from body motions. Therefore, a horse cartilage explant model was developed. The explant model was used to ensure that the FiberGel graft can effectively integrate into a defect, and that the horse chondrocytes and MSC being encapsulated in the FiberGel can survive, proliferate and produce the needed ECM.

Full-thickness defects (d=5 mm) were created in the trochlea cartilage plugs (d=10 mm) of horse specimens in organ culture. FiberGel made of 4 and 20 μm microfibers were mixed with horse MSC, which mimicked cells from bone marrow, or chondrocytes (at 30 million cells per cm$^3$), filled to the defects, and solidified by blue light (390~400 nm). The explants are cultured under established in-vitro conditions and the tissue analyzed. The cultures were maintained for up to 4 weeks. The implants' mechanical properties were measured using compression tests. The binding between host cartilage and implant was examined by push-out tests using a loading station. Tissues formed in the scaffolds was analyzed by immunohistology and compared with native femoral cartilage tissues.

Horse chondrocytes were obtained by digesting the articular cartilage, which was harvested from mature horse knee joints. They were trypsinized and then encapsulated in fibers with diameters of 4 μm and 20 μm after one passage expansion, and photo-crosslinked into two groups of samples. Samples were cultured in chondrocytes growth medium for 42 days to examine the influence of fiber meshwork on long-term cell behavior of Horse chondrocytes. Horse MSCs were centrifuged from a horse bone marrow concentrate. They were trypsinized and then encapsulated in fibers with diameters of 4 μm and 20 μm after one passage expansion and crosslinked into two groups of samples. Samples were cultured in chondrogenic medium for 42 days to examine whether 3D fiber architecture can have an impact on cell fate decision of horse stem cells. For evaluation, the analysis followed the recommendations of outcomes measurement from FDA guidelines, and was used to determine what combination of fiber architecture and cell source is more conductive to cartilage matrix formation.

Another in-vitro study examined whether the conclusion drawn from the first in-vitro study worked in an in-vitro explant model, which can better resemble the in-vivo environment compared with in-vitro scaffold-only model. To create such model, Horse osteochondral explants were harvested from horse knee joints, defects with diameters of 5 mm were punched in the middle of cartilage of the osteochondral explants. Cells were encapsulated in fibers with diameters of 4 μm and 20 μm after one passage expansion and injected into the defects. After the defects were filled by cell-fiber mixture, the samples were formed by photo-crosslinking the fibers in the defects. This in-vitro explant study served as the pivot to prepare for the following in-vivo study and provided more data for outcome analysis recommended by FDA guidelines.

To evaluate the conductivity of fiber architecture in promoting cartilage matrix formation, based on FDA guidelines recommendations, the following experimental data was collected, mechanical outcomes (including the Young's moduli of bulk sample, proteoglycan together with scaffolds, collagen fibril networks), biochemical analysis (GAG content), histology images, immunofluorescence images, and gene transcriptional expressions of SOX9, aggrecan, type I, II, X collagen. Such data helps determine which fiber architecture and cell source should be used in the in-vivo study.

Horse Cell Based In-Vitro Studies

Experimental Design

Fiber Architecture.

Two groups with randomly oriented fibers a. 20 μm group: fiber diameter D=20 μm, meshwork stiffness 25-30 KPa b. 4 μm group: fiber diameter D=4 μm, meshwork stiffness 25-30 KPa Fibrous Matrix.

Fibers were first rehydrated, mixed well with cells, then photo crosslinked into cylindrical matrices, with thickness of 2.5 mm and diameters of 5 mm.

Cell Source.

Horse chondrocytes were obtained by digesting the articular cartilage, which was harvested from mature horse knee joints. Horse MSCs were centrifuged from horse bone marrow concentration. Both chondrocytes and MSCs were cultured for one passage, followed by trypsinization and encapsulation.

Seeding Density.

20 million cells per cm$^3$

Cell Culture.

Samples were cultured in chondrogenic differentiation medium (for Horse MSCs encapsulated samples) or in chondrocytes growth medium supplemented with TGF-β (for Horse chondrocytes encapsulated samples) for 42 days.

Data Collection

Unconfined compression test was used for mechanical properties of bulk matrices, including instantaneous compression modulus, equilibrium compression modulus. Finite element modeling and curve fitting algorithm were applied to fit the numerical simulation results to experimental data to de-couple the Young's moduli of collagen networks and proteoglycan hydrogels from the mechanical data of bulk matrices. Histology staining was used for visualization of collagen and GAG deposition. Immunofluorescence was used for identification of type I, II, X collagen deposition, as well as aggrecan deposition.

Biochemical analysis, Dimethylmethylene Blue Assay (DMMB), was used to quantify GAG production in each sample. RT-PCR was used to quantify the gene transcriptional expression for cell phenotype evaluation.

Results

Thick Microfilaments and Horse Chondrocytes were the Best Combination to Increase Mechanical Strengths Unconfined compression tests were used to measure the changes of samples' mechanical properties. In each measurement, a preload of 0.02 N was applied and maintained for 300 sec. The samples were then compressed by 10% strain at a rate of 3% per second and was maintained at 10% strain for a 1000 sec, a wait time to allow the sample to relax. From each relaxation curve, the peak stress was used to calculate the instantaneous modulus and equilibrium stress for the equilibrium modulus.

Figure 14A:
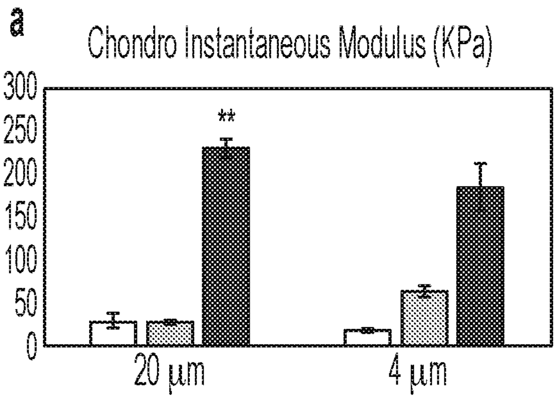
FIGS. 14A-14D show that fiber meshwork promotes increases in compression moduli of bulk samples. Instantaneous modulus of 20 μm chondrocyte group and 4 μm chondrocyte group (FIG. 14A), 20 μm MSC group and 4 μm MSC group (FIG. 14B). Day 1, day 21 and day 42. Equilibrium modulus of 20 μm chondrocyte group and 4 μm chondrocyte group (FIG. 14C) and 20 μm MSC group and 4 μm MSC group (FIG. 14D), obtained from unconfined compression tests. Significance: *p<0.05, **p<0.01, n=3.

Significantly increased mechanical strengths were observed in all matrices (D=20 μm or 4 μm, horse chondrocytes or MSC embedded). For the matrices made of thick fibers (D=20 μm), embedding horse chondrocytes on day 1 caused the instantaneous moduli to dramatically increase by about 200 kPa, from 30 KPa on day 1 to about 230.2 KPa on day 42 (FIG. 14A). Decreasing the filament diameter from 20 μm to 4 μm caused the horse chondrocytes to increase the instantaneous moduli by a lower extent, from 25 KPa on day 1 to about 184.2 KPa on day 42 (FIG. 14A).

Figure 14C:
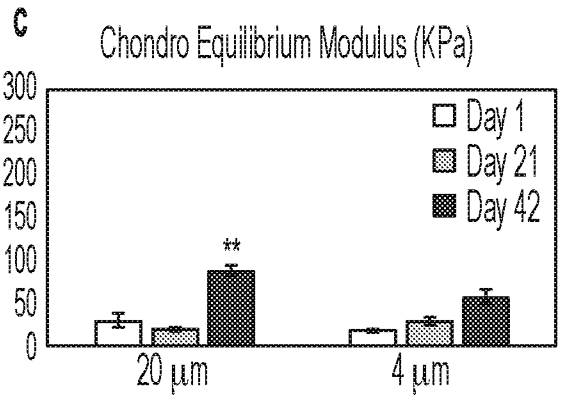
Figure 14B:
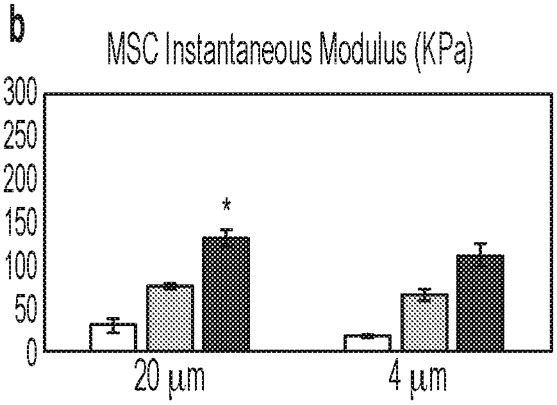

Changing the cell type to horse MSC instead of using chondrocytes led to generally lower instantaneous moduli at day 42. From day 1 to day 42, the horse MSC increased the instantaneous moduli of 20-μm matrices to about 131 KPa, while increasing the instantaneous moduli of 4-μm matrices to about 111.2 KPa (FIG. 14B).

Figure 14D:
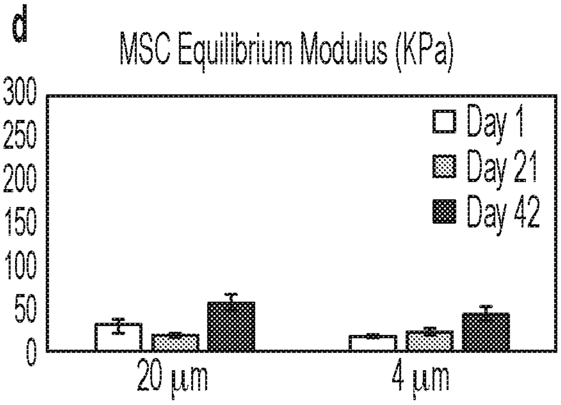

The equilibrium moduli also increased from day 1 to day 42 in all groups. The equilibrium moduli of the 20-μm/chondrocyte group increased from about 30 KPa at day 1 to about 87.4 KPa on day 42 (FIG. 14C), and the equilibrium moduli of the 4-μm/chondrocyte group increased from about 25 KPa to about 57.3 KPa on day 42. In contrast to the chondrocyte groups, the equilibrium moduli of MSC groups increased by much lower extents. In day 42 days, the equilibrium moduli of the 20-μm/MSC group and that of the 4-μm/MSC group only increased to about 56.5 KPa and 43.6 KPa, respectively (FIG. 14D).

Overall, in this model it was found that the thicker microfilaments (D=20 μm) promote the increase of instantaneous modulus and equilibrium modulus. The horse chondrocytes were found more capable of increasing the mechanical strength of the microfilament matrices, in comparison with the horse MSC.

Matrix Architecture (as Characterized by Microfilament Diameter and Pore Size) Influences GAG Production Biochemical assay was conducted to measure the amount of the cell-produced glycosaminoglycan (GAG), a key component of articular cartilage, following existing protocols. The GAG content in native horse cartilage was measured for control. Given that the filament matrices were made of denatured collagen (gelatin), which is subject to cell-digestion and remodeling, biochemical assay was not used to measure the amount of collagen content, as such measurement cannot distinguish cell-produced collagen from the collagen of the initial matrix.

Figure 15A:
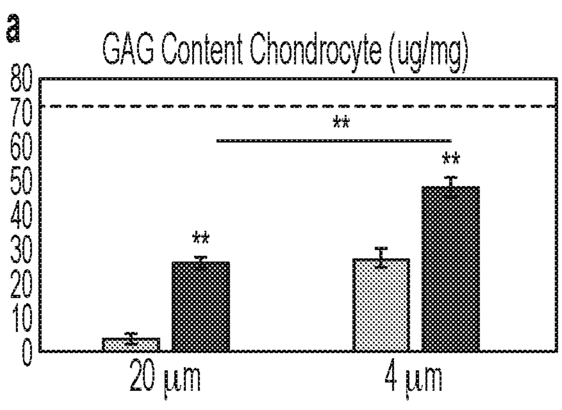
FIGS. 15A-15B shows that fiber architecture influences GAG production. GAG content of 20 μm chondrocyte group and 4 μm chondrocyte group (FIG. 15A), 20 μm MSC group and 4 μm MSC group, at day 21 and day 42 (FIG. 15B). Significance: **p<0.01, n=3.
Figure 15B:
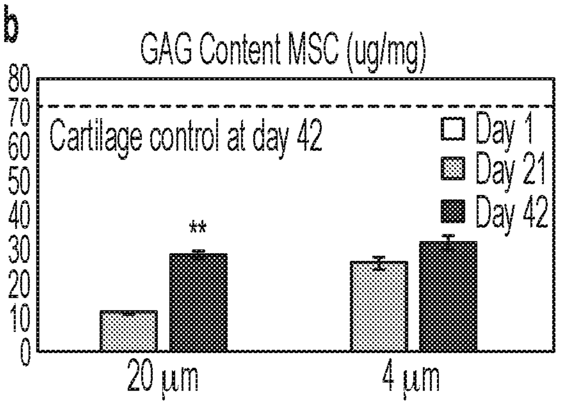

Interestingly, although the above unconfined compression tests suggested that the samples with 20-μm filaments (or 50 to 100 μm pores) performed better than samples with 4 μm filaments (or 10 to 40 μm pores), the GAG assay showed an opposite trend. For both horse chondrocyte and MSC, the cells embedded in the 4-μm group were found to produced significantly higher amount of GAG than cells in the 20-μm group (FIGS. 15A-15B). All groups showed significant increases in GAG content at the later stage (from day 21 to day 42), except the 4-μm/MSC group, in which the GAG amount plateaued.

The weight of GAG in the 20-μm/chondrocyte group reached 26.3 μg per mg of total sample dry weight, which is about 36.3% of GAG content in the native horse cartilage (control group, cultured in-vitro for 42 days). In contrast to the thicker filament group (20-μm), in 42 days the GAG content in the 4-μm/chondrocyte group reached about 48 μg/mg, about 66.5% of the GAG in the native horse cartilage (FIG. 15A).

The above results show that matrix architecture (as characterized by microfilament diameter and pore size) significantly affect the amount of GAG produced by chondrocytes. In contrast, when the cell type was changed to horse MSC, the influence of matrix architecture on GAG production became less obvious. On day 42, the GAG contents of the 20-μm/MSC group and 4-μm/MSC group both reached about 40% of the GAG content of native cartilage (39.5% and 44.3%, respectively) (FIG. 15B).

Matrix Architecture Regulates Cartilage-Like ECM Deposition

Figure 16:
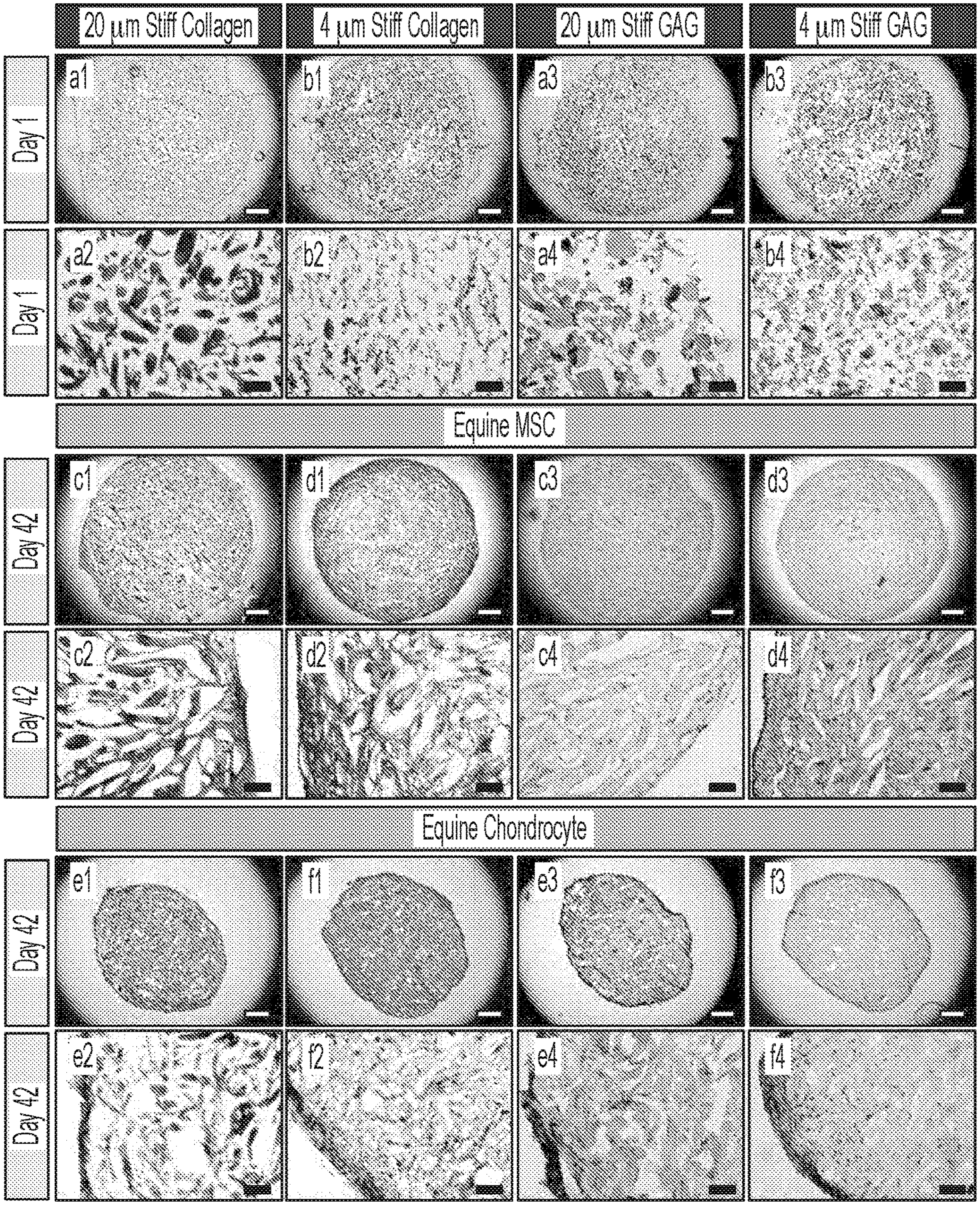
FIG. 16 shows that the fiber architecture determines the deposition density of cartilage matrix. Representative Masson's Trichrome Staining for collagen images of 20 μm groups with a1) low magnification and a2) high magnification at day 1; 4 μm groups with b1) low magnification and b2) high magnification at day; c1-c2) 20 μm MSC group at day 42, d1-d2) 4 μm MSC group at day 42, e1-e2) 20 μm chondrocyte group at day 42, and f1-f2) 4 μm chondrocyte group at day 42. Representative Safranin O and fast green staining (red stains for GAG) images of a3-a4) 20 μm groups at day 1, b3-b4) 4 μm groups at day 1, c3-c4) 20 μm MSC group at day 42, d3-d4) 4 μm MSC group at day 42, e3-e4) 20 μm chondrocyte group at day 42, and f3-f4) 4 μm chondrocyte group at day 42. Scale bars: 50 μm in images with high magnification, 500 μm in images with low magnification.

Masson's Trichrome Staining was used to visualize the collagen contents, and Alcian Blue was used to stain GAG contents. FIG. 16 shows the representative images of histology staining, stains for collagen in Masson's Trichrome Staining, and the stains for GAG in Alcian Blue staining. Microfilaments of FiberGel were stained red stain. The trichrome staining showed that all groups perform significantly increased collagen and GAG contents from day 1 to day 42. This shows that the microfilament matrices support cartilage-like matrix deposition. The density of collagen and GAG was found observably higher in the matrices of 4-μm filaments than in the matrices of 20-μm filaments. Comparisons between the chondrocyte and MSC groups, showed more ECM deposition in chondrocyte groups than their MSC counterparts at day 42.

Matrix Architecture Regulates Cell Phenotype

Figure 17:
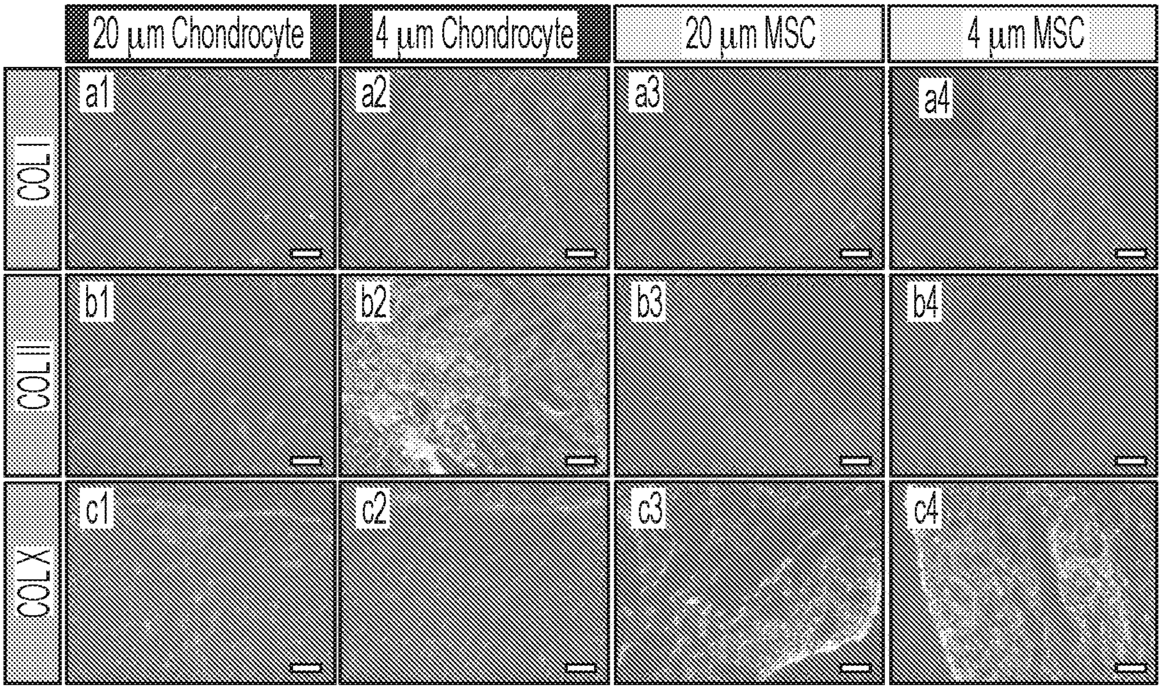
FIGS. 17A-17C show that the fiber architecture regulates chondrogenic differentiation of hMSC. Expressions of chondrogenic related genes, including a) type I collagen b) type II collagen c) type X collagen d) aggrecan, normalized to the expressions of housekeep gene. n=3.

Immunofluorescence was used to identify the type of collagen produced by horse chondrocytes or MSCs cultured in different fiber architecture. Chondrocytes in 4 μm group expressed strong intensity of type II collagen, but weak intensities of type I or X collagen (FIG. 17, panels a2, b2, c2). While chondrocytes in 20 μm group showed stronger intensity of type X collagen compared with either type I or type II collagen (FIG. 17, panels a1, b1, c1). By contrast, MSCs in both 4 μm and 20 μm groups expressed strong intensity of type X collagen, and little intensities of type I and type II collagen (FIG. 17, panels a3, b3 c3 and panels, a4, b4, c4).

Discussion

Micro-Filamentous Network Promotes Interconnected Cartilage-Like Matrix Formation by Horse Chondrocytes and MSCs The above results showed that the 3D micro-filamentous network, which resembles the native ECM, promote interconnected ECM formation (collagen and GAG) by horse chondrocytes and MSCs, in both short-term (21 days) and long-term (42 days). This was evidenced by the significant increase of instantaneous and equilibrium moduli in the samples in 42 days. Histology staining showed that the gaps between micro filaments became gradually occupied by collagen and GAG in 42 days. Biochemical assays also showed that the microfilament matrices support the production of GAG contents by both horse chondrocytes and MSC. In all groups, the dry-weight ratios of GAG were shown to exceed one third of the dry-weight ratio of GAG in native horse cartilages.

In contrast to the microfilament matrix, i.e. FiberGel, homogeneous and linear elastic hydrogels that are often used for tissue engineering are suboptimal for the cell production of new ECM. The hydrogel network presents nanometer-size pores to cells, and this dense mesh restricts the cell-production of ECM to the peripheral region of cells, leading to small volumes of isolated ECM while preventing the formation of interconnected ECM network. As a result, cells in hydrogel-based matrices often fail to produce a strong bulk matrix that is needed for load-bearing tissue such as cartilages.

Most hydrogel matrices also limit cells to a linear elasticity environment and do not allow cells to perform matrix-remodeling. In contrast, it was shown that the microfilament matrix enables human MSC to perform contractile-remodeling, which helps maintain round cell morphology, down-regulate YAP-based signaling and promotes chondrogenic phenotype.

Horse MSC and Chondrocyte Show Different Response to Fiber Architecture

Horse chondrocyte groups showed better results in terms of mechanical outcomes, biochemical outcomes, and cell phenotype, compared with their MSC counterparts. This could be caused by the intrinsic difference between horse chondrocytes and MSCs, for example, the sensitivity to fiber architecture could be different for different cell type.

Naturally, in the injured cartilage, chondrocytes in lesions tended to express type X collagen, which is associated with hypotrophy and calcification, instead of type II collagen. In this study, collagen deposition of both MSC groups consisted mainly of type X collagen, indicating the mechanosensing itself is not enough to overturn this nature of hypertrophic differentiation. While such hypertrophy nature was suppressed in 4 μm group, as horse chondrocytes were sensitive to fiber architecture mediated mechanosensing.

The driving force that leads to such difference in cell sensitivity to mechanosensing was associated with the environmental changes resulted from long-time ECM deposition and cell remodeling of fiber matrix. In FIG. 16, the most striking difference between horse chondrocyte and horse MSC groups was the morphological change of samples, MSC groups generally maintained the initial diameter and circular cross-section, but chondrocyte groups contracted into irregular cross-section. This comparison shows horse chondrocytes were more active than MSCs and could explain why horse chondrocytes were more sensitive to mechanosensing.

There was similar density of GAG deposition in 20 μm chondrocyte group, 4 μm and 20 μm MSC groups, but higher content of GAG in 4 μm chondrocyte group, which is the only group that expressed more type II collagen than either type I or type X collagen. This suggests, apart from initial fiber architecture, the ECM deposition in long-term could be a major contributor to effective mechanosensing that can eventually regulate cell phenotype.

Human and Horse Stem Cells Show Different Sensitivity to Fiber Architecture

Previous study showed the fiber architecture can regulate the chondrogenic differentiation of human MSCs, but this study showed the same architecture was not enough to overturn the cell fate decision of horse MSC. To fully understand such difference would require expertise across a variety of fields, as well as more relevant studies. However, this study shows the importance to build up models for translational studies that can match characteristics of human cells.

In conclusion, in this study, horse chondrocytes and MSCs were used to test the conductivity of fiber architecture to cartilage matrix formation. It was found that 4 μm fiber architecture was more conductive, and horse chondrocytes were the better cell source.

In-Vitro Osteochondral Explant Model

Experimental Design

Fiber Architecture.

Two groups with randomly oriented fibers a. 20 μm group: fiber diameter D=20 μm, meshwork stiffness 25-30 KPa b. 2 μm group: fiber diameter D=2 μm, meshwork stiffness 25-30 KPa Fibrous Matrix.

The horse explant model was created by punching defects (with diameter of 5 mm) in the cartilage of osteochondral explants. Fibers were first rehydrated, mixed well with cells, then injected to fill the defects, followed by photocross-linked in the defects.

Cell Source.

Horse chondrocytes were obtained by digesting the articular cartilage, which was harvested from mature horse knee joints. Horse MSCs were centrifuged from horse bone marrow concentration. Both chondrocytes and MSCs were cultured for one passage, followed by trypsinization and encapsulation.

Seeding Density.

20 million cells per $cm^3$

Cell Culture.

Samples were cultured in chondrogenic differentiation medium (for Horse MSCs encapsulated samples) or in chondrocytes growth medium supplemented with TGF-β (for Horse chondrocytes encapsulated samples) for 42 days.

Data Collection

Indentation tests were conducted. Finite element modelling and curve fitting algorithm were applied to fit the numerical simulation results to experimental data to decouple the Young's moduli of collagen networks and proteoglycan hydrogels from the mechanical data of bulk matrices. Push-out tests were conducted to evaluate the integration strength between implants and cartilage tissues. Histology staining was used for visualization of the integration between implants and cartilage tissues, as well as collagen and GAG deposition. Immunofluorescence was used for identification of type I, II, X collagen and aggrecan deposition at the interface between implants and cartilage tissues. Biochemical analysis, Dimethylmethylene Blue Assay (DMMB), was used to quantify GAG production in each sample. RT-PCR was used to quantify the gene transcriptional expression for cell phenotype evaluation.

Results

Microfilament Matrices Promote Integration Between Implants and Host Cartilage

Figure 18A:
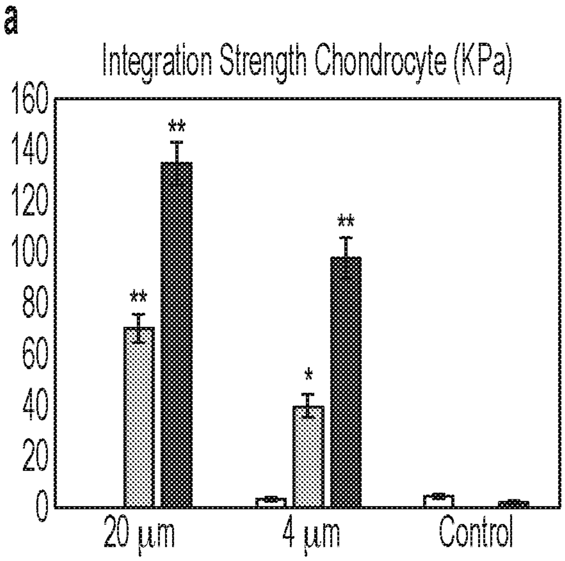
FIGS. 18A-18B show that fiber meshwork promotes integration strength of implants with surrounding cartilage. Integration strength of 20 μm chondrocyte group and 4 μm chondrocyte group (FIG. 18A), 20 μm MSC group and 4 μm MSC group, at day 1, day 21 and day 42 (FIG. 18B), measured by push-out tests. Significance: *p<0.05, **p<0.01, n=3.
Figure 18B:
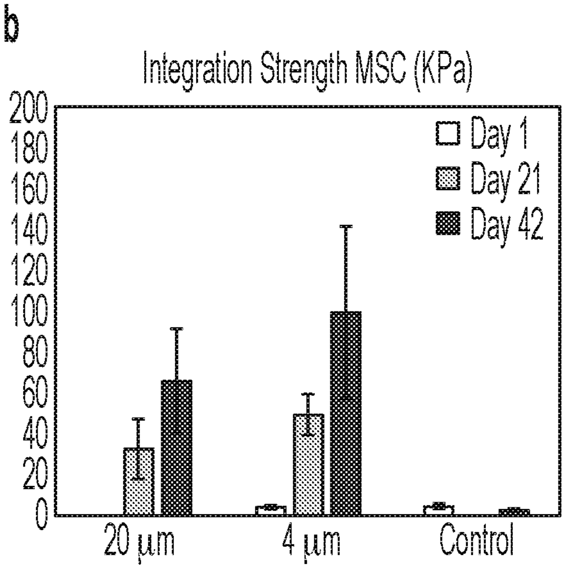

Push-out tests were conducted to examine integration strength between implants (cells encapsulated in fiber meshwork) and adjacent cartilage of the osteochondral explants. Briefly, the subchondral bone of explants was sectioned off, leaving the cartilage alone with implants in the defects. The cartilage was then fixed to the loading stage. A cylindrical indenter with diameter of 4.75 mm (slightly smaller than the diameter of defect, 5 mm) was used to push implants in the center. The load applied on indenter increased gradually, until implants failed to stay in the defect and fell off from cartilage. The maximum load, along with the thickness of cartilage, was recorded. The integration strength was calculated directly by the ultimate stress (maximum load divided by the area of side wall). The integration strength represented how strong the bonding between implants and cartilage was, as shown in FIGS. 18A-18B. It increased from almost zero (0.63 KPa and 3.49 KPa on average for 20 μm and 4 μm group, respectively) at day 1, to over 120 KPa for 20 μm chondrocyte group (averagely 135.27 KPa), around 100 KPa for 4 μm chondrocyte group (averagely 98.08 KPa), at day 42 (FIG. 18A). The MSC groups also showed significant increases in integration strength for 42 days, to an average of 66.57 KPa for 20 μm MSC group and 99.69 KPa for 4 μm MSC group, although there were huge variations among the data at day 42 (FIG. 18A). As comparison, the control group, which was created by culturing a cylindrical cartilage in the defect of the same osteochondral explant model, maintained the low integration strength throughout the 42 days.

Figure 19:
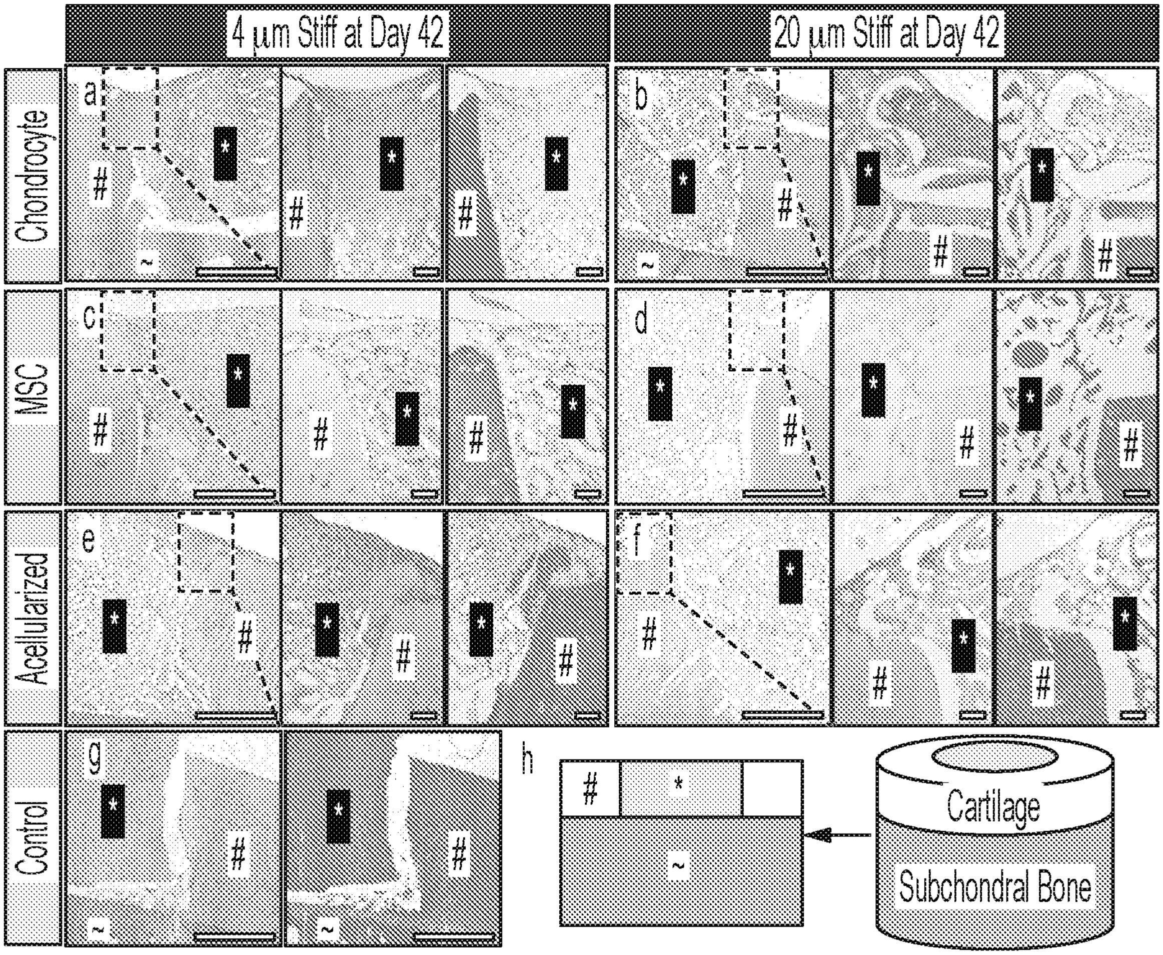
FIG. 19 shows that fiber architecture influences integrative cartilage matrix deposition. Representative Masson's Trichrome Staining (blue stains for collagen), Safranin O and fast green staining images of 4 μm chondrocyte group (panel a), 20 μm chondrocyte group (panel b), 4 μm MSC group (panel c), 20 μm MSC group (panel d), 4 μm acellular group (panel e), 20 μm acellular group (panel f), and control group, at day 42 (panel g). The schematic of in-vitro osteochondral explant model (panel h), * refers to the implants, # refers to host cartilage, refers to subchondral bone. Scale bars: 100 μm in images with low magnification, 1 mm in images with high magnification.

Fiber Architecture Influences Cartilage Matrix Deposition at the Interfaces Between Implants and Surrounding Cartilage Masson's Trichrome Staining was used to visualize the collagen deposition, Safranin O and fast green was used to distinguish GAG from subchondral bones. FIG. 19 shows the representative images of histology staining, stains for collagen in Masson's Trichrome Staining, while staining for GAG was done with red stain and stains for collagen in Safranin O and fast green staining. The host cartilage and implant contain both GAG and collagen. In the 4-μm/chondrocyte group, cartilage-like matrix, particularly GAG components, was found at the interface between implants and surrounding cartilage, showing that the implant and host cartilage were integrated by the new ECM that horse cells produced. (FIG. 19, panel a). In most 4-μm/chondrocyte samples, this integration zone extended from the surface of cartilage/implant to about 1 mm below the surface but did not reach the subchondral bone. In contrast to the 4-μm/chondrocyte group, in the 20-μm/chondrocyte group the integration zone were most limited to the proximity of the cartilage surface of cartilage (FIG. 19, panel b). In the control group, in which the defect was inserted with a cartilage plug, it was found that the chondrocytes fail to bridge the gap (which was about 200 μm) between the cartilage plug and host cartilage in 42 days (FIG. 19, panel g).

For MSC groups, it was also found that the 4-μm/MSC group presented more ECM produced at the implant/host interface than the 20-μm/MSC group (FIG. 19, panels c and d). However, different from the chondrocyte groups, the implant/host integration was shallow and close to the surface. This is in consistence with the push-out results, which showed that the chondrocyte-based groups preformed significantly stronger implant/host binding than MSC-based groups.

To find out whether the implant/host integration was formed solely by encapsulated cells or as a result of the infiltration of native chondrocytes, samples of acellular implant were prepared, in which microfilaments (D=20 μm or 4 μm) without cells were filled and crosslinked in the defects. In the 4-μm/acellular group, from histology sizable areas of integration zone at the implant/host interface were observed (FIG. 19, panel e). This indicate the host chondrocytes contribute to the integration of 4-μm filament-based matrix. In contrast, such integration was not observed in the 20-μm/acellular group (FIG. 19, panel f).

In all groups, the deposition of cartilage-like matrix was found to take place mainly on the superficial layers for all groups (up to 1-mm deep), with most dense collagen and GAG components formed on the surface.

Figure 20:
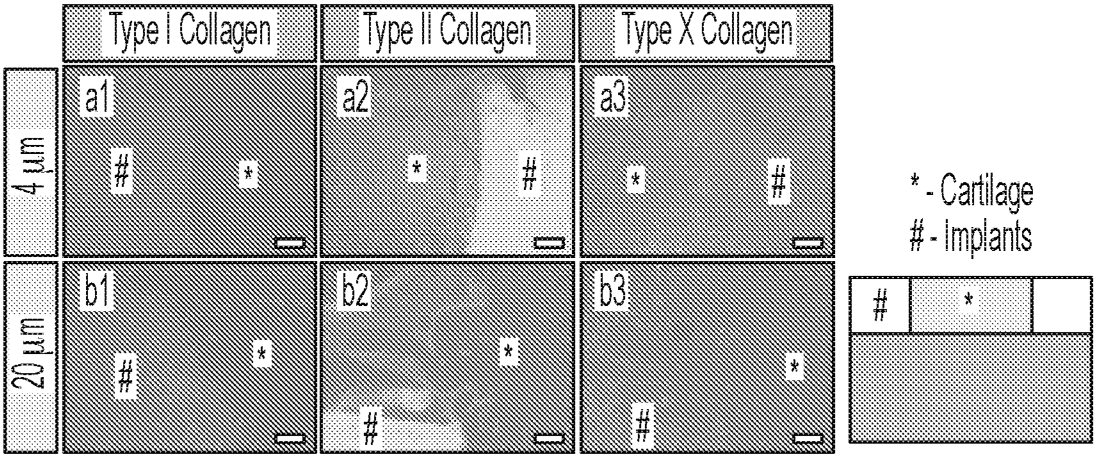
FIG. 20 shows integrative cartilage matrix contains mostly type II collagen. Immunofluorescence of a1) type I (green), a2) type II (green), a3) type X (green) collagen in the implant-cartilage integration of 4 μm chondrocyte group at day 42, and b1) type I (green), b2) type II (green), b3) type X (green) collagen in the implant-cartilage integration of 20 μm chondrocyte group at day 42, nuclei is blue. Scale bars: 100 μm.

The deposited matrix bridging the implants and host cartilage consisted of mainly type II collagen, as shown by immunofluorescence images of chondrocyte groups (FIG. 20, panels a2 and b2). In contrast, type I and type X collagen (which are associated with cartilage scars and calcified cartilages, respectively) had intensities that was indistinguishable from background (FIG. 20, panel a1, b1, a3 and b3). Sizable area of type II collagen deposition was observed in the 4-μm/chondrocyte group, while the type II collagen deposition was limited to the superficial zone of the 20-μm/chondrocyte group.

Microfilament Matrices Promote the Increase of Mechanical Strength

Having established that horse chondrocytes provide significantly better implant/host integration, we evaluated the effect of microfilament architecture on the bulk mechanical strength of the chondrocyte-based groups.

Indentation measurements were conducted to evaluate several mechanical parameters of implants. In brief, a 0.2 mm indent depth (the cartilage thickness was measured after indentation when the subchondral bone was sectioned off) at a rate of 3% strain per second was then applied, followed by a 1000 s relaxation hold to equilibrium, the stress relaxation curve was recorded for the following curve fitting process. To do so, a finite element model was built to simulate the mechanical response of the compression test (the stress relaxation curve), and Levenberg-Marquardt algorithm, a nonlinear least-squares method, was developed. By iterations of finite element analysis (FEA), the Young's moduli was estimated from the base scaffolds and the base-matrix components (which is denoted as E), the re-enforcement to Young's moduli by microfiberous components (which is denoted as ksi), and the change of permeability (which is denoted as κ) due to cell-produced GAG components. Samples were modeled as a 3° wedge of a cylindrical disk with axisymmetric boundary conditions. The material of this model was defined as biphasic, consisting of a neo-Hookean solid phase (with Young's modulus of E) with an isotropic fiber distribution (with Young's modulus of ksi). The material was also defined as having a strain independent permeability as an approximation of the average permeability across strains. The loading platen was modeled as an impermeable rigid body. To estimate the values of E, ksi and κ, the Levenberg-Marquardt algorithm was performed to fit the stress relaxation curve obtained in experiments (divided by 120 for 3° wedge). By iteration, the algorithm searched values and combinations of these three parameters to minimize the square root of the differences between FEA calculated the stress relaxation curve and experiment data. The calculated E and ksi described the strength of load bearing components, presumably provided by the new collagen and GAG contents. Given that the calculated κ is proportional to the square of mesh size, this data could be used to roughly estimate the strength of proteoglycan-GAG components that cells produced in each sample.

Figure 21A:
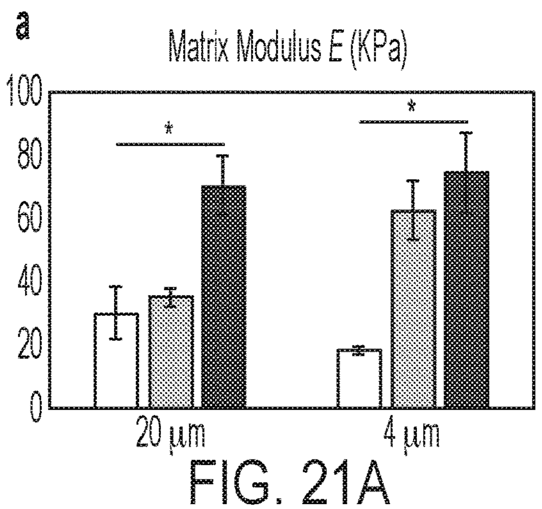
FIGS. 21A-21D shows that fiber meshwork promotes the growth of mechanical properties of implants. Young's modulus of base matrix of 20 μm 4 μm chondrocyte group (FIG. 21A), and Young's modulus of fiber re-enforcement of 20 μm 4 μm chondrocyte group, at day 1, day 21 and day 42 (FIG. 21B). Permeability, which is proportional to the square of mesh size, of 20 μm 4 μm chondrocyte group (FIG. 21C), schematic of indentation tests and curve fitting process (FIG. 21D). Significance: *p<0.05, n=3.
Figure 21B:
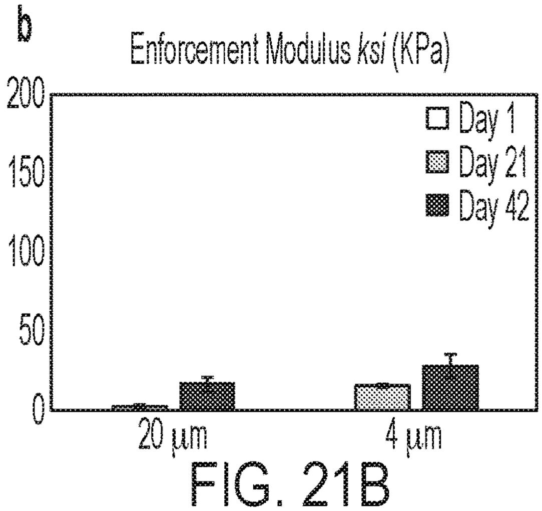
Figure 21D:
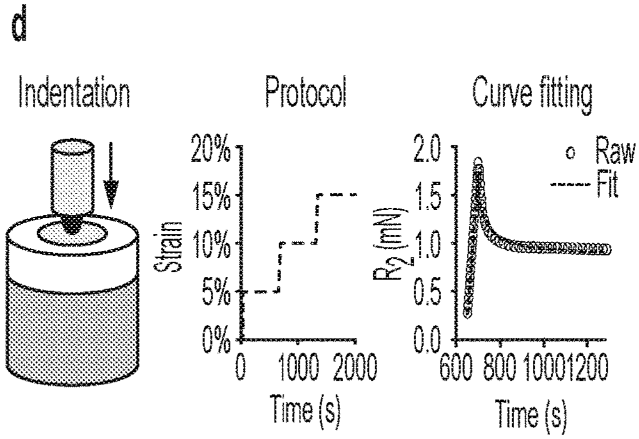
Figure 21C:
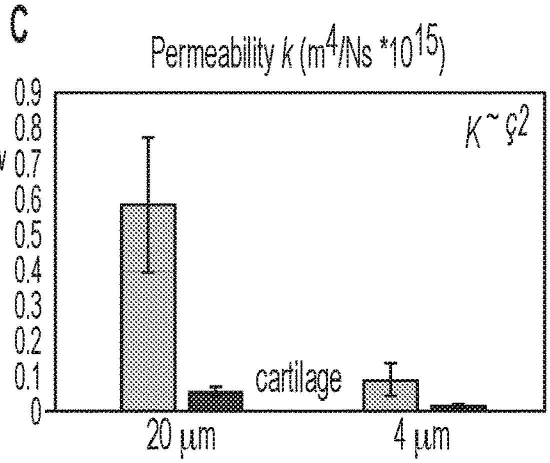

Based on estimation, the strength base matrix (E) increased significantly for both 20-μm and 4-μm group from day 1 to day 42 (FIG. 21A). The combined mechanical moduli of new base matrix components and the original microfilaments (which gradually degraded) increased from about 30 KPa to 70 KPa for the 20-μm group and increased from about 25 KPa to 74 KPa for the 4-μm group. In contrast to the base matrix' moduli, the strength of fibrous components (ksi) was found to increase by a smaller extent. New fibrous components were estimated to increase the overall mechanical strength by about 16.41 KPa for the 20-μm group and 28.05 KPa for the 4-μm group. The strengthening of fibrous components became insignificant for the later stage (from day 21 to day 42) (FIG. 21B). It was also found that permeability of implant became significantly lower, which signifies the formation of denser GAG network (FIG. 21C).

Matrix Architecture Influences GAG Production

Figure 22A:
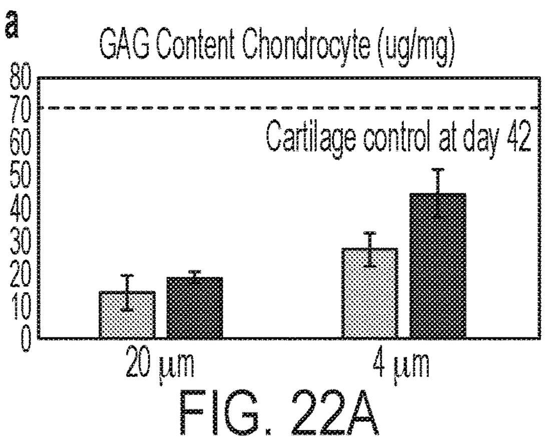
FIGS. 22A-22B shows that Fiber architecture influences GAG production. GAG content of 20 μm chondrocyte group and 4 μm chondrocyte group (FIG. 22A), 20 μm MSC group and 4 μm MSC group, using in-vitro osteochondral explant model, at day 21 and day 42, n=3 (FIG. 22B).
Figure 22B:
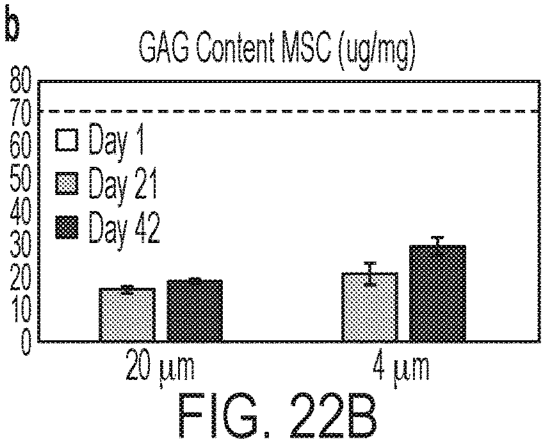

Biochemical assay was used to measure the amount of GAG components in cartilage matrix. This shows that the amount of GAG continued to increase from day 1 to day 42 (FIGS. 22A-22B). For the chondrocyte groups, in 20-μm group the GAG content (weight per dry sample weight) reached 18.6 μg/mg (which is about 25.7% of GAG content in horse cartilage), and in the 4-μm group the GAG content reach 44.8 μg/mg (which is about 62% of the GAG content in the host horse cartilage (FIG. 22A).

The MSC-based groups showed a similar amount of GAG production in comparison with the chondrocyte group: 18.6 μg/mg in the 20-μm/MSC group (25.7% of GAG content in the host cartilage) and 29.5 μg/mg in the 20-μm/MSC group (40% of GAG content in the host cartilage) (FIG. 22B). Overall, higher GAG content was found in the matrices made of thin filaments and cell-size pores (the 4-μm group) in comparison with the matrices with thick filament and larger pores (the 20-μm group).

Discussion

Meeting the Unmet Clinical Need: Implant Host-Cartilage Integration

Despite the intensive work on using biomaterials to repair articular cartilage, successful integration between implanted materials and surrounding cartilage has rarely been reported. However, a strong integration strength is necessary for long-term repair efficacy, as the implants constantly experience the compressive and shear loads, weak integration of implants with surrounding tissue would result in high failure possibility. Therefore, integrative repair has long been established as a critical index in regulatory documents, such as the FDA guidelines.

Cartilage defects are difficult to fill. The shape of defects is often irregular, and the defect's boundary often present abnormal biochemical components and cell population of abnormal phenotypes. Hypocellularity in cartilage at the boundary of surgical debridement was shown in adult rabbits and minipigs. Similarly, when drilling defects in osteochondral explant model, the up-regulated apoptosis was found in superficial zone chondrocytes as far as 400 mm from the defect margin, as well as necrosis in all zones immediately adjacent to the defect. The hypocellularity, apoptosis and necrosis would eventually reduce the chondrogenic capacity of cells of both side at the interface, as well as the chance of cartilage to integrate with repair tissue.

Widely used biomaterials for cartilage replacements, which include various types of scaffolds, are often in solid phase when transplanting into defects. It is extremely challenging for the cells to bridge up gap between implanted biomaterials and surrounding cartilage. Hydrogel-based tissue filler have been used to achieve a seamless defect filling. However, most hydrogels contain nanometer-scale mesh that hinders cell migration, preventing cells and ECM components from the implant and the host to integrate. To promote integration, chemicals that capable of partially digesting cartilages, such as FGF-18, sprifermin (Sennett, M. L. et al. Journal of Orthopaedic Research®, 2018. 36(10): p. 2648-2656) and collagenase (Qu, F. et al Nature Communications, 2017. 8(1): p. 1780) have been tested for cartilage repair. At the implant/host interface, sprifermin has been shown to promote chondrocyte proliferation, cartilage matrix biosynthesis, and improve the cartilage-to-cartilage integration. Collagenase can digest the cartilage matrix, enabling the free chondrocytes to fuse into gaps between implanted and host cartilage and synthesize new cartilage matrix to fill the gaps. However, these methods are suboptimal, as the safety of using reagents cable of disintegrating cartilages for repair cartilages can raise serious concerns to the FDA.

The FiberGel-based, 3D microfilament matrix provides a potential solution to facilitate the implants to integrate with surrounding cartilage. First, at the tissue level, cell encapsulated fibers have a physical property that is like gels, they can change their morphology depending on containers. The un-crosslinked fibers can pass through a needle (down to 22-gauge), photo-crosslinked, and turned into a scaffold to completely fill a defect of an arbitrary shape. Second, at the cellular level, micrometer-scale mesh size enables cell infiltration or migration, allowing cell proliferation and new cartilage matrix synthesized at the interface between fibers and cartilage. More importantly, the fiber architecture provides inductive microenvironment to limit the possibility of fibrocartilage formation. Here it was tested the effectiveness of this approach by an osteochondral explant model. Increased integration strength, as well as the gradually deposition of cartilage matrix at the implant/host interface, was found in 4-μm/chondrocyte group. Together, the results showed a strong integration between fibers and cartilage. The above results verify the efficacy of the 3D microfilament matrix for cartilage repairing.

Optimizing Cellular Microenvironment to Promote Integration of Implant

The experimental data showed that the filament diameters and pore size if the matrix affect the morphology of cell-produced ECM at the implant/host interface. Based on histology images, architecture made of 4-μm filaments induced larger integration depth than the ones made of 20-μm filaments. The 4-μm filaments also promote the formation of denser new ECM at the implant/host interface. The microfilaments matrices used enabled a fine-tuning of cellular microenvironment, such that desired cellular behaviors, e.g. implant integration, can take place.

Promoting cartilage-associated cell phenotypes is another challenge for implant/host integration. Due to the loss of biophysical cues from ECM, cells at the gap between implant and host cartilage tend to produce cartilage scar, which is subject to continual degradation for long term. The immunohistology results showed that using the microfilament matrix at the implant/host interface can promote the cell production of type II collagen and GAG, showing the formation of cartilage-like matrix. The above results showed that fiber architecture influences integrative matrix formation. It has been demonstrated from the previous in-vitro tests that both chondrocytes and MSCs in sub-cellular size fibrous mesh produced denser cartilage matrix, as cells in a such microenvironment tend to create contractile deformation, which promote a round cell morphology, down-regulate the YAP/TAZ based mechanotransduction signaling, and thus promote chondrogenesis.

Host cells invasion to the implant is another important factor for achieving implant/host integration. Acellular implant groups were included to investigate whether or to what extent the chondrocytes from the host cartilage contribute to the implant integration. The results showed that, when the 4-μm microfilaments were used, host chondrocytes migrated into the implant matrix and produced ECM to seal the gap at the interface. The 20-μm microfilaments also enable host cell invasion, but the production of ECM at the interface became less in both density and volume. It is believed that the use of 4-μm microfilament matrix provided a bridge that is need for host cell infiltration and migration. In comparison with the 20-μm microfilament matrix, the 4-μm filament provides more surface area per volume (due to the thinner diameter) to host cell migration and the production of ECM.

The above result again demonstrates the advantage of microfilament matrix over the traditional hydrogel. Since hydrogels are crosslinked polymers, the typical mesh size of hydrogels is less than 1 μm, substantially below the typical size of cells (10-20 μm), cellular size. Studies elsewhere showed that cell migration become severely impeded when the mesh size area below 5 μm (Rowat, A. C. et al., Journal of Biological Chemistry, 2013. 288(12): p. 8610-8618; Harada, T. et al., J Cell Biol, 2014. 204(5): p. 669-682; Denais, C. M. et al, Science, 2016. 352(6283): p. 353-358; Wolf, K., M. et al., J Cell Biol, 2013. 201(7): p. 1069-1084).

Therefore, due to the lack of mesh space for cell invasion and migration, using hydrogel-based matrix for cartilage implant is prone to poor implant/host integration. In contrast, the microfilament matrices made of FiberGel have an average mesh size that is above 20 μm, which enables the cell mobility that is needed to achieve cell invasion and implant integration.

The above problem of hydrogel reveals the fact that there is an optimal mesh size for cartilage implant. Such mesh size would be large enough to enable cell migration but small enough to provide the cell confinement that promote cartilage-like cell bioactivities. Although it shown that using thinner microfilaments (ex: D=4 μm) promote denser ECM production, for clinical applications, one should try to identify an optimal filament size that simultaneously facilitate cell migration/invasion and promotes chondrogenic phenotypes.

Aside from implant integration, using this horse explant model it was again verified that the architecture of microfilament matrices can be optimized for cartilage-like matrix production in the implant. It is verified by indentation-based mechanical tests, as well as the finite-element model analysis to estimate the change of permeability. Permeability is proportional to the square mesh size, and decreased permeability indicates new ECM synthesized within the microfilament matrix, which reduces the initial mesh size and impairs water diffusion through the matrix. Both 20-μm and 4-μm groups showed decreased permeability in 42 days, while the permeability of the 4-μm groups, which provided 10 to 40 μm mesh size, became significantly lower than the 20-μm group (which provided 100 to 200 μm mesh size), suggesting that significantly more ECM was produced in the 4-μm groups than in the 20-μm groups. This estimation was verified by biochemical assay, which showed the 4-μm groups provided more GAG. Histology also confirmed that the 4-μm groups produced thicker and denser collagen and GAG matrix at the interface. The above results again demonstrate that the microarchitecture of microfilament matrices, as characterized by filament diameter and mesh size, can be tuned for optimal cartilage-like tissue production.

Cartilage Defect is an Asymmetric Environment for Cartilage-Like Formation

Previously in the in-vitro model, it was showed that the ECM deposition in the matrices was symmetric, which more matrix deposition at the external region of the sample. In contrast, here in the explant model, it was found that the cell-production of ECM was mostly located by the open side of the implant, while the new ECM was significantly less in both density and volume at the side near the subchondral bone. Although large area of cartilage matrix was found at implant-cartilage interface or superficial layer, very limited deposition of cartilage matrix was seen in the middle region of implants and the region near subchondral bone. This limited ECM deposition could be a result of inadequate nutrition supply because liquid diffusion occurred only via the surface. Upon long term culture, the diffusion may decorate due to the formation of denser ECM near the surface, which lowers the permeability. The asymmetry of cartilage matrix deposition in osteochondral explant model highlights the importance of using explant model to verify the conclusion summarized from in-vitro tests, the explant model can provide a similar environment such as diffusion, cartilage-implant communication, which cannot be mimicked in the simple cell-fiber in-vitro models.

Conclusion

In this study, an horse osteochondral explant model was built to prepare for the following translational large animal studies. Horse chondrocytes and MSCs were used to test the formation of integrative cartilage matrix between implant and surrounding cartilage. Again, it was found that 4 μm fiber promoted such integrative cartilage matrix formation, and horse chondrocytes were the better cell source. Acellular fiber matrix was also included to see the contribution of cell infiltration from host cartilage and found the integration in 4 μm acellular group.

Example 5: Horse Cadaver Studies

Figure 23:
FIG. 23 depicts application of FiberGel to a horse joint (horse cadaver): (panel a) Joint preparation including hair removal. (panel b) Make incision. (panel c) Expose the trochlea groove. (panel d) Create a full-thickness defect (d=15 mm). (panel e) Fill the defect with FiberGel. (panel f) Expose FiberGel to blue light (390~400 nm wavelength) and make the FiberGel's microfibers inter-crosslinked. (panels g and h) Cover crosslinked FiberGel with collagen sheet and suture the collagen sheet to surrounding cartilage.
Figure 24:
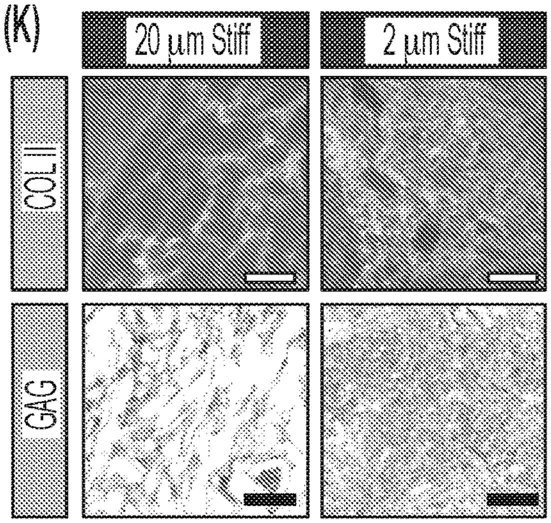
FIG. 24 shows that FiberGel with 20 μm and 2 μm microfibers promote cartilage tissue formation by human chondrocytes.
Figure 25:
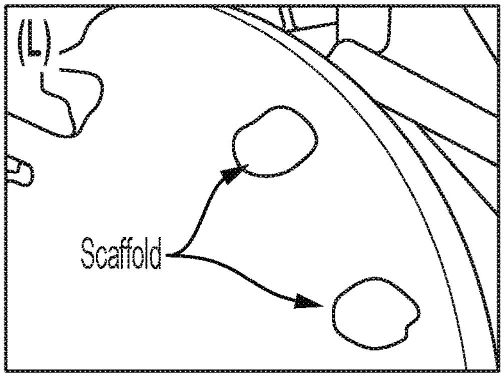
FIG. 25 is an image showing scaffold during horse cadaver testing.
Figure 26:
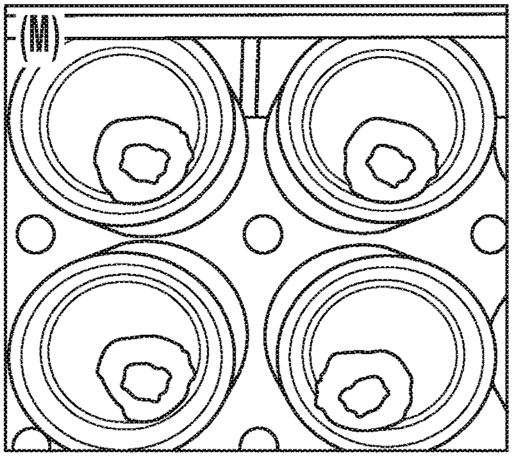
FIG. 26 is an image of horse cartilage explant.

Joints of horse cadaver were used as model to help develop the protocols for using FiberGel in the operation room (FIG. 23). Horse stifle joint was dissected, and patella flipped aside to expose the trochlea groove. Full-thickness defects (d=15 mm) were created in the trochlea cartilage. The defected were conditioned with PBS for 5 to 10 minutes, which swelled the edge of the defect and stabilized its geometry. The swelling form a slightly undercut in the defect, which helps trap the implant inside the defect. FiberGel made of 4 or 20 μm microfibers were hydrated with PBS with 10% serum and 0.1% photoinitiator, at about 1:10 fiber-PBS weight ratio, and filled to the defects. The applied FiberGel was covered with sterilized transparent slides, which blocked oxygen and enhanced crosslinking, and solidified by hand-held light source (390~400 nm, 1 mW/cm$^2$, 5 min). Finally, to protect the crosslinked FiberGel, the crosslinked FiberGel was covered with a standardized collagen sheet that is used for ACI, and the sheet was then fixed to the surrounding cartilage by suturing.

To mechanically challenge the scaffolds implant, the horse's patella was flipped back into the trochlea groove and was pushed back and forth along the trochlea groove for 30 cycles. The scaffolds were intact and remained inside the defects. Protocols for synthesis and application of FiberGel were fine-tuned based on these results.

Example 6: In Vitro Study Using Human Cells

The followed studies were conducted to test the efficacy of FiberGel using human chondrocytes and human MSC, as models for ACI implant and microfracture.

Studying the Effect of Fiber Diameter:

FiberGel made of subcellular scale (d=4 μm) and cellular scale (d=20 μm) microfibers were tested on vitro studies using human chondrocytes (which mimics ACI procedure), which were encapsulated in FiberGel scaffolds and cultured in chondrocyte expansion media for six weeks. While the fibers of different diameters both support the production of hyaline cartilage (Col-II positive) by chondrocytes, the results suggest that these fibers provide different advantages for cartilage repair. FiberGel made of 4 μm microfibers provide larger inner surface area for cell engraftment, proliferation and denser matrix production. In contrast, 20 μm fibers provide more space for cell migration and could facilitate host/implant integration. It is expected that the horse cartilage explant model, in which host cartilage is in presence, will tell which type of FiberGel is more optimal.

Effect of Fiber Stiffness on Implant's Geometric Stability.

The effects of FiberGel stiffness on cartilage formation were also tested using human chondrocytes. In six weeks, scaffolds made of microfibers of moderate stiffness (~20 kPa) were found to support cell production of ECM while providing sufficient mechanical strength to sustain the original geometry (in width and height). In contrast, microfibers of extremely low stiffness (~0.5 kPa) could not sustain the geometry of scaffolds. In three weeks, chondrocytes in the scaffold made of the 0.5 kPa, soft microfibers gradually shrank the scaffold by about ⅔ of the original size (width and height). The causes of shrinking were found to be (1) the contraction of chondrocyte-produced collagen; and (2) the internalization and digestion of soft microfibers by chondrocytes.

Enumerated Embodiments

The following enumerated embodiments are provided, the numbering of which is not to be construed as designating levels of importance.

Embodiment 1 provides an injectable scaffold comprising:

a plurality of unclad microfibers; and, a diluent solution.

Embodiment 2 provides the injectable scaffold of embodiment 1, wherein the microfibers comprise unclad shavings from a shaved stretch-and-fold ring comprising a plurality of microfibers clad in a sheath.

Embodiment 3 provides the injectable scaffold of embodiment 1, wherein the microfibers are gelatin microfibers.

Embodiment 4 provides the injectable scaffold of embodiment 1, wherein the microfibers comprise one or more selected from the group consisting of: natural polymers, synthetic polymers, and combinations thereof.

Embodiment 5 provides the injectable scaffold of embodiment 4, wherein the natural polymers comprise one or more selected from the group consisting of: gelatin, collagen, elastin, fibrin, fibrinogen, laminin, dextran, silk protein, chitosan, alginate, heparin, heparin sulfate, and laminin, and combinations thereof.

Embodiment 6 provides the injectable scaffold of embodiment 4, wherein the synthetic polymers comprise one or more selected from the group consisting of: polyethylene glycol, polycaprolactone, polylactic acid, polyglycolic acid, polylactic-glycolic acid, Teflon™, Nylon™, polycarbonate, polyamide, polystyrene, polypropylene, polyester, and combinations thereof.

Embodiment 7 provides the injectable scaffold of embodiment 1, wherein the diluent solution comprises one or more solutions selected from the group consisting of saline, water, media, and buffered saline.

Embodiment 8 provides the injectable scaffold of embodiment 1, wherein the plurality of microfibers comprises microfibers having uniform diameter.

Embodiment 9 provides the injectable scaffold of embodiment 8, wherein the diameter of each microfiber varies from about 0.1 μm to about 100 μm.

Embodiment 10 provides the injectable scaffold of embodiment 8, wherein the scaffold comprises pores that are about 5 times to about 10 times larger than the diameter of the microfibers forming the scaffold.

Embodiment 11 provides a method of repairing a soft tissue defect in a subject, the method comprising:

(a) obtaining a microfiber stretch-and-fold ring comprising a plurality of microfibers and a cladding;
(b) shaving the stretch-and-fold ring into a plurality of chips;
(c) dissolving the cladding from the chips by contacting the chips with an uncladding solution to unclad the microfibers;
(d) hydrating the unclad microfibers with a hydrating solution, thereby forming a paste;
(e) introducing a plurality of cells into the paste, thereby forming a seeded paste;
(f) loading the seeded paste into a syringe; and,
(g) injecting the seeded paste into a region of interest.

Embodiment 12 provides the method of embodiment 11, wherein the microfibers comprise one or more selected from the group consisting of: natural polymers, synthetic polymers, and combinations thereof.

Embodiment 13 provides the method of embodiment 12, wherein the natural polymers comprise one or more selected from the group consisting of: gelatin, collagen, elastin, fibrin, fibrinogen, laminin, dextran, silk protein, chitosan, alginate, heparin, heparin sulfate laminin, and combinations thereof.

Embodiment 14 provides the method of embodiment 12, wherein the synthetic polymers comprise one or more selected from the group consisting of: polyethylene glycol, polycaprolactone, polylactic acid, polyglycolic acid, polylactic-glycolic acid, Teflon™, Nylon™, polycarbonate, polyamide, polystyrene, polypropylene, polyester, and combinations thereof.

Embodiment 15 provides the method of embodiment 11, wherein the cladding comprises polycaprolactone (PCL) cladding.

Embodiment 16 provides the method of embodiment 11, wherein the uncladding solution comprises one or more selected from the group consisting of: acetone, chloroform, hexane, ethanol, methanol, pentane, methylcyclohexane, ethane, dimethyl sulfoxide, ethyl ether, perfluoropentane, perfluoromethylcyclohexane, hexafluoroethane, perfluoro-1,3-dimethylcyclohexane, perfluoromethyldecalin, and/or combinations thereof.

Embodiment 17 provides the method of embodiment 11, further comprising:

(h) crosslinking the seeded paste.

Embodiment 18 provides the method of embodiment 17, wherein the crosslinking comprises crosslinking with one or more selected from the group consisting of: visible light, UV light, glutaraldehyde, BDDE, enzymes, click chemistry, and combinations thereof.

Embodiment 19 provides the method of embodiment 11, wherein the hydrating solution comprises one or more selected from the group consisting of: saline, media, buffered saline, phosphate-buffered saline, sterile water, and/or combinations thereof.

Embodiment 20 provides the method of embodiment 11, wherein the plurality of cells comprises one or more selected from the group consisting of: chondrocytes, pluripotent cells, stem cells, and fibroblasts.

Embodiment 21 provides the method of embodiment 11, wherein the seeded paste is injected using a 22 g needle.

Embodiment 22 provides the method of embodiment 11, wherein the chips have a thickness of about 200 μm.

Embodiment 23 provides the method of embodiment 11, wherein the chips have a length of from about 200 μm to about 5000 μm.

Embodiment 24 provides the method of embodiment 11, wherein the subject is a mammal.

Embodiment 25 provides the method of embodiment 24, wherein the subject is human.

Embodiment 26 provides a kit comprising:

the injectable scaffold of claim 1, a plurality of cells in solution, and a sterile syringe and needle.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of repairing a soft tissue defect in a subject, the method comprising:

(a) obtaining a microfiber stretch-and-fold ring comprising a plurality of microfibers and a cladding;

(b) shaving the stretch-and-fold ring into a plurality of chips which comprise a length of from about 200 μm to about 5000 μm;

(c) dissolving the cladding from the chips by contacting the chips with an uncladding solution to obtain unclad the microfibers;

(d) hydrating the unclad microfibers with a hydrating solution, thereby forming a paste;

(e) introducing a plurality of cells into the paste, thereby forming a seeded paste;

(f) loading the seeded paste into a syringe; and, (g) injecting the seeded paste into a region of interest, wherein the region of interest is a soft tissue defect.

2. The method of claim 1, wherein the microfibers comprise one or more selected from the group consisting of: natural polymers, synthetic polymers, and combinations thereof.

3. The method of claim 2, wherein the natural polymers comprise one or more selected from the group consisting of: gelatin, collagen, elastin, fibrin, fibrinogen, laminin, dextran, silk protein, chitosan, alginate, heparin, heparin sulfate, laminin, and combinations thereof; and, wherein the synthetic polymers comprise one or more selected from the group consisting of: polyethylene glycol, polycaprolactone, polylactic acid, polyglycolic acid, polylactic-glycolic acid, polycarbonate, polyamide, polystyrene, polypropylene, polyester, and combinations thereof.

4. The method of claim 1, wherein the cladding comprises Polycaprolactone (PCL) cladding.

5. The method of claim 1, wherein the uncladding solution comprises one or more selected from the group consisting of: acetone, chloroform, hexane, ethanol, methanol, pentane, methylcyclohexane, ethane, dimethyl sulfoxide, ethyl ether, perfluoropentane, perfluoromethylcyclohexane, hexafluoroethane, perfluoro-1,3-dimethylcyclohexane, perfluoromethyldecalin, and combinations thereof.

6. The method of claim 1, wherein the method further comprises crosslinking the seeded paste with one or more selected from the group consisting of: visible light, ultraviolet (UV) light, glutaraldehyde, 1,4-butanediol diglycidyl ether (BDDE), enzymes, click chemistry, and combinations thereof.

7. The method of claim 1, wherein the hydrating solution comprises one or more selected from the group consisting of: saline, media, buffered saline, phosphate-buffered saline, sterile water, and combinations thereof.

8. The method of claim 1, wherein the plurality of cells comprises one or more selected from the group consisting of: chondrocytes, pluripotent cells, stem cells, and fibroblasts.

9. The method of claim 1, wherein the seeded paste is injected using a 22 gauge needle.

10. The method of claim 1, wherein the chips have a thickness of about 200 μm.

11. The method of claim 1, wherein the subject is a human.

* * * * *